(12) United States Patent
Cathomen et al.

(10) Patent No.: US 11,319,580 B2
(45) Date of Patent: May 3, 2022

(54) METHOD FOR CHARACTERIZATION OF MODIFICATIONS CAUSED BY THE USE OF DESIGNER NUCLEASES

(71) Applicants: Albert-Ludwigs-Universitaet Freiburg, Freiburg (DE); Deutsches Krebsforschungszentrum Stiftung des oeffentlichen Rechts, Heidelberg (DE)

(72) Inventors: Toni Cathomen, Freiburg (DE); Giandomenico Turchiano, Freiburg (DE); Georges Blattner, Freiburg (DE); Gianni Monaco, Ariano Irpino (IT); Melanie Boerries, Heidelberg (DE); Geoffroy Andrieux, Heidelberg (DE)

(73) Assignees: Albert-Ludwigs-Universitaet Freiburg, Freiburg (DE); Deutsches Krebsforschungszentrum Stiftung des oeffentlichen Rechts, Heidelberg (DE)

(*) Notice: Subject to any disclaimer, the term of this patent is extended or adjusted under 35 U.S.C. 154(b) by 0 days.

(21) Appl. No.: 17/277,236

(22) PCT Filed: Sep. 19, 2019

(86) PCT No.: PCT/EP2019/075101
§ 371 (c)(1),
(2) Date: Mar. 17, 2021

(87) PCT Pub. No.: WO2020/064478
PCT Pub. Date: Apr. 2, 2020

(65) Prior Publication Data
US 2021/0317514 A1 Oct. 14, 2021

(30) Foreign Application Priority Data
Sep. 25, 2018 (EP) .................................. 18196438

(51) Int. Cl.
*C12Q 1/6848* (2018.01)
*C12Q 1/6869* (2018.01)

(52) U.S. Cl.
CPC ......... *C12Q 1/6848* (2013.01); *C12Q 1/6869* (2013.01)

(58) Field of Classification Search
CPC ................ C12Q 1/6848; C12Q 1/6869; C12Q 2525/161; C12Q 2525/191; C12Q 2563/179
See application file for complete search history.

(56) References Cited

U.S. PATENT DOCUMENTS

2018/0135080 A1* 5/2018 Barradeau ........ C12Q 2523/303
2018/0346977 A1* 12/2018 Alt ...................... C12Q 1/6869

FOREIGN PATENT DOCUMENTS

WO WO 2016/081798 A1 5/2016
WO WO 2018/129368 A2 7/2018

OTHER PUBLICATIONS

Shengdar Q. Tsai et al., "GUIDE-seq Enables Genome-Wide Profiling of Off-Target Cleavage by CRISPR-Cas Nucleases", *Nature Biotech*, vol. 33 (2): 187-197 (Dec. 2014).
Winston X. Yan et al., "BLISS is a Versatile and Quantitative Method for Genome-Wide Profiling of DNA Double-Strand Breaks", *Nature Comm.*, vol. 8: 15058 (1-9) (May 2017).
Daesik Kim et al., "Digenome-seq: Genome-Wide Profiling of CRISPR-Cas9 Off-Target Effects in Human Cells", *Nature Methods*, vol. 12 (3): 237-243 (Mar. 2015).
Shengdar Q. Tsai et al., "CIRCLE-seq: A Highly Sensitive In Vitro Screen for Genome-Wide CRISPR-Cas9 Nuclease Off-Targets", Nature Methods, vol. 14 (6): 607-614 (May 2017).

* cited by examiner

*Primary Examiner* — David C Thomas
(74) *Attorney, Agent, or Firm* — Smith Patent, LLC; Chalin A. Smith

(57) ABSTRACT

Disclosed is a method for high-throughput detection of genome-wide modifications in a nucleic acid genome obtained from a cell or tissue caused by the activity of a designer nuclease comprising the following steps:
a) Extraction of the genomic DNA from cells that were exposed to a designer nuclease under conditions which allow the designer nuclease to introduce a DNA double-strand break (DSB) in the genomic DNA of the cell,
b) fragmentation of the nucleic acid to obtain random fragments,
c) performing an end repair in order to obtain blunt ends,
d) ligation with a linker comprising a sequence complementary to a so called "linker primer",
e) performing a first nucleic acid amplification reaction with a "linker primer" and a so called "ON-target primer", whereby one primer is located upstream and one primer is located downstream of the on-target site, wherein at least one decoy primer is present in the reaction mixture,
f) performing a second nucleic acid amplification reaction whereby so called "nested primers" are added to the reaction mixture, whereby one primer is complementary to the on-target locus and one primer complementary to the linker sequence,
g) performing a further nucleic acid amplification reaction whereby at least one code containing primers are added to the reaction mixture,
h) sequencing of the nested and barcoded amplification product, and
i) aligning the sequenced products with suitable bioinformatic means to a reference sequence to identify a chromosomal location that contains a genomic modification based on at least one DNA double strand break.

12 Claims, 11 Drawing Sheets
Specification includes a Sequence Listing.

Figure 1. Schematic of CAST-Seq.
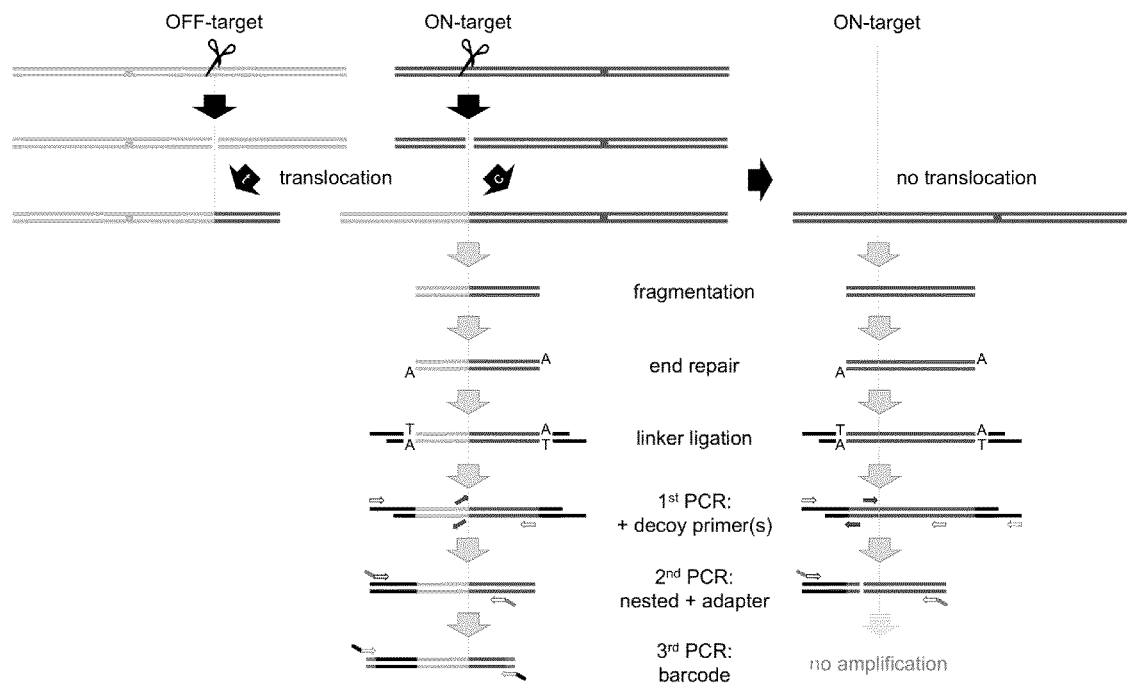
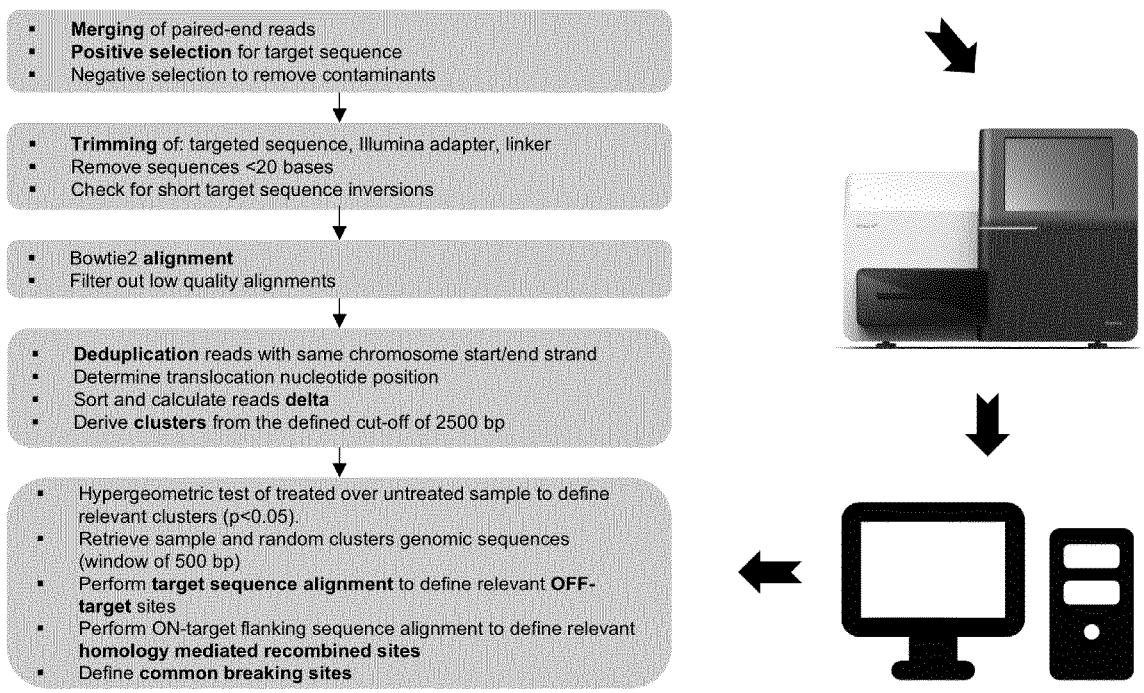

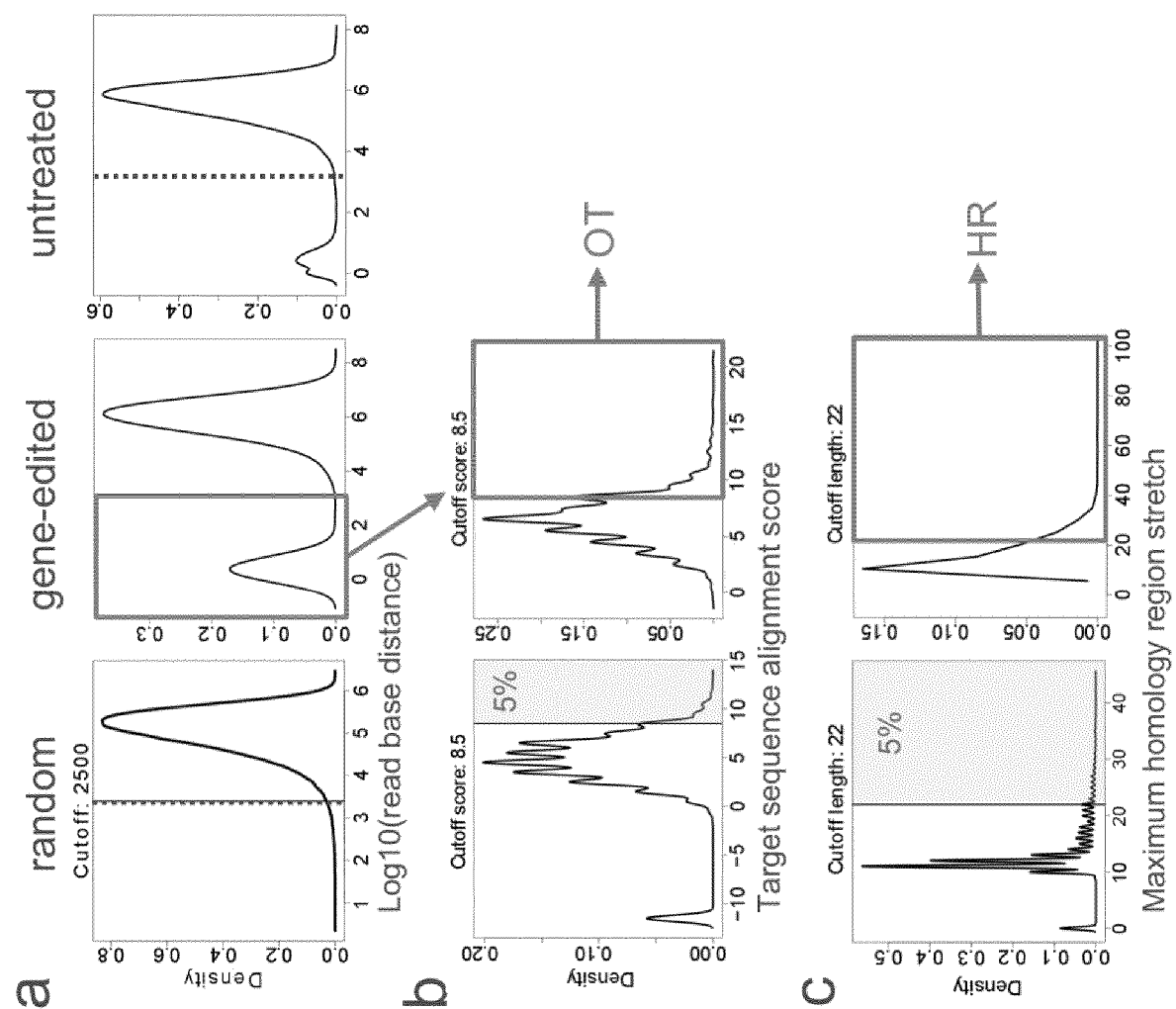
Figure 2. Bioinformatical definition of categories.

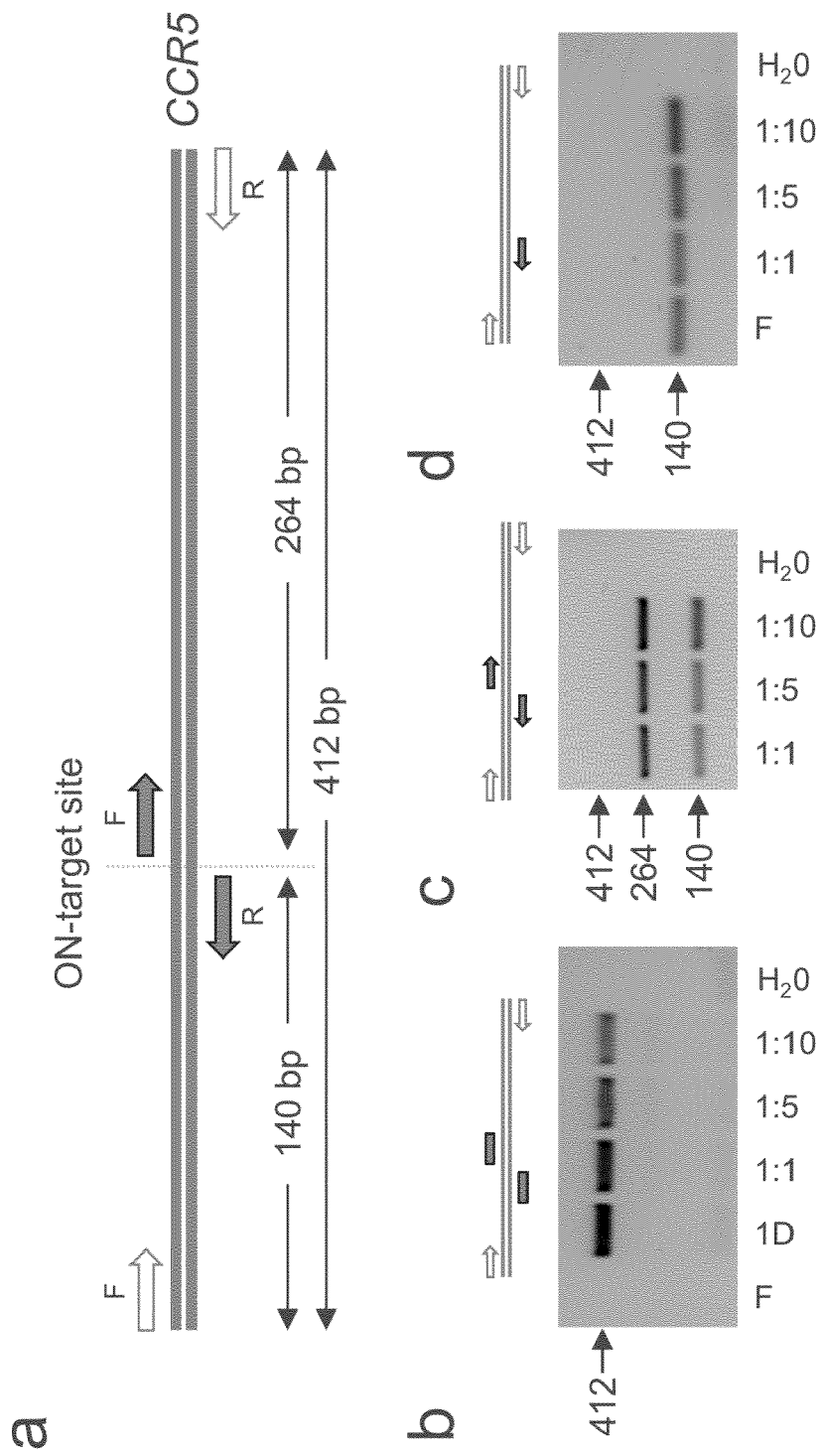
Figure 3. Effect of decoy oligonucleotide primers

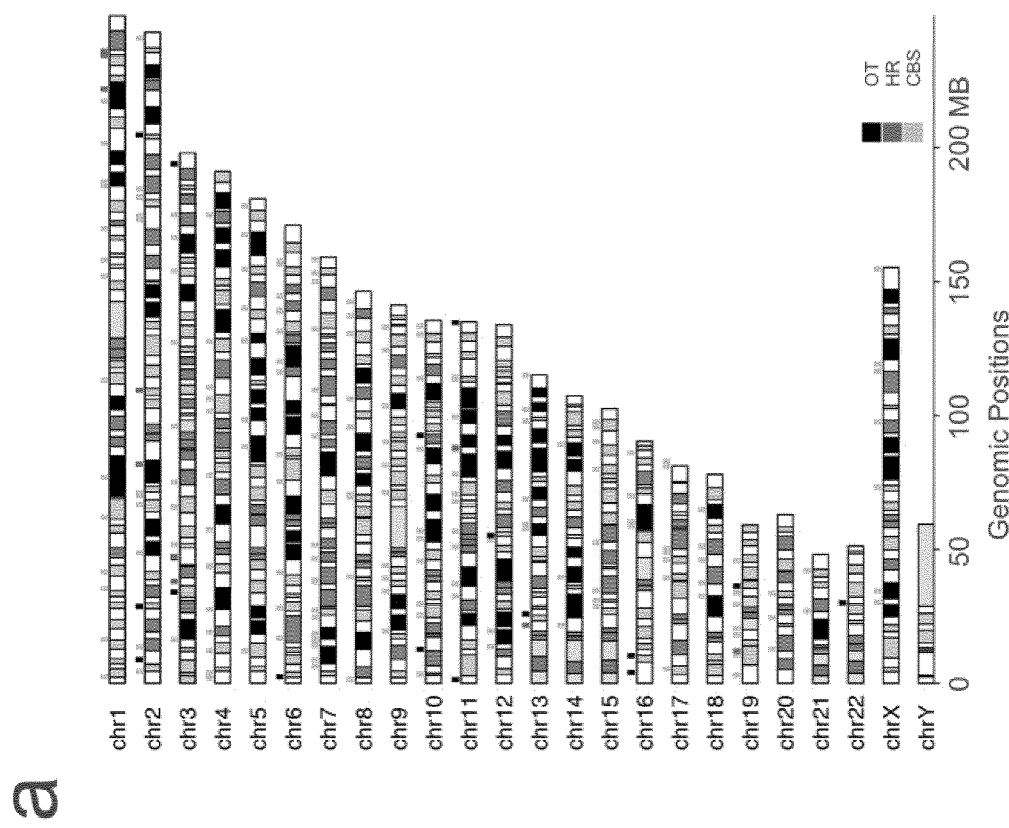
Figure 4. Genomic modifications mapped by CAST-Seq in gene edited human hematopoietic stem cells

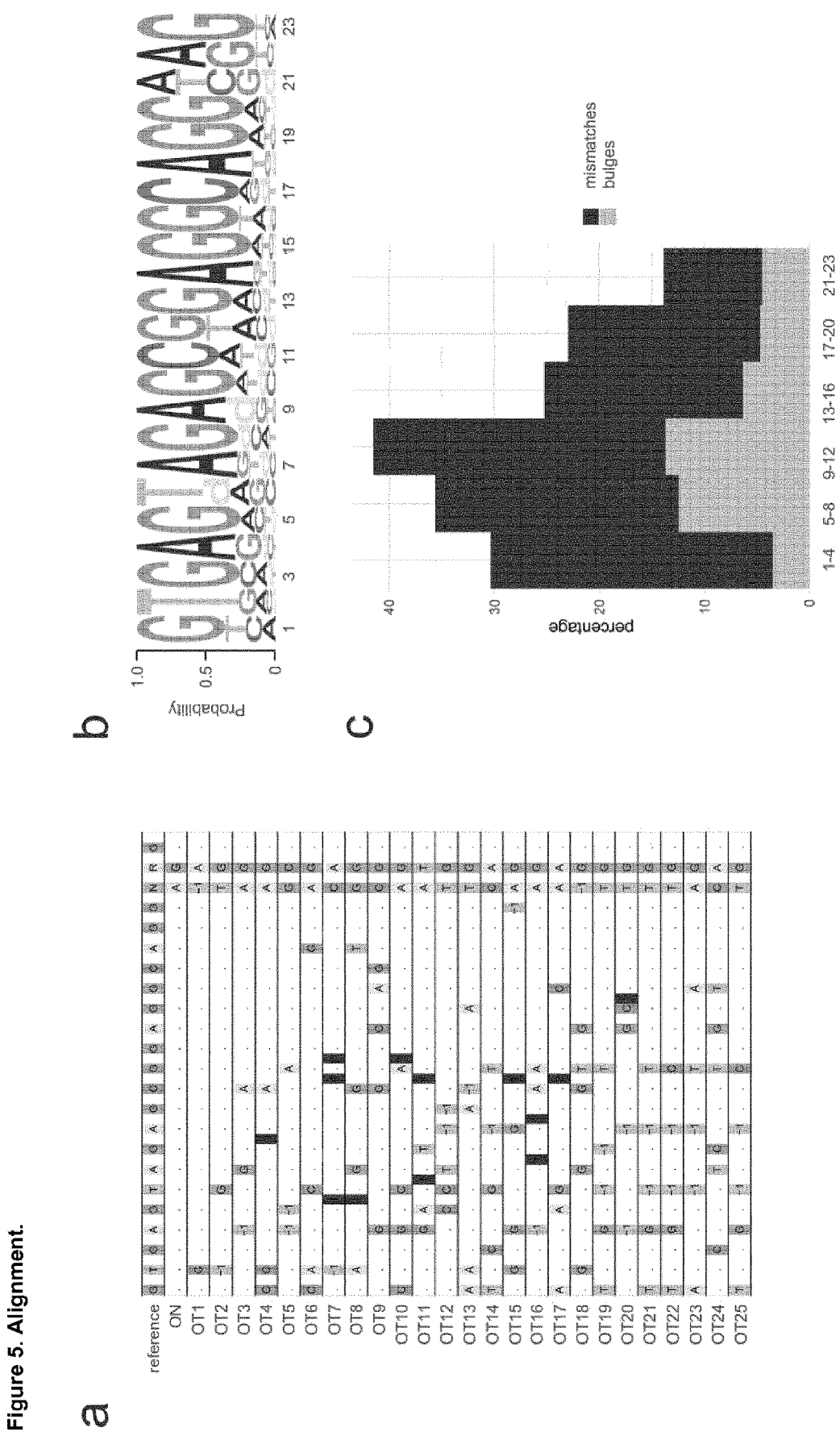
Figure 5. Alignment.

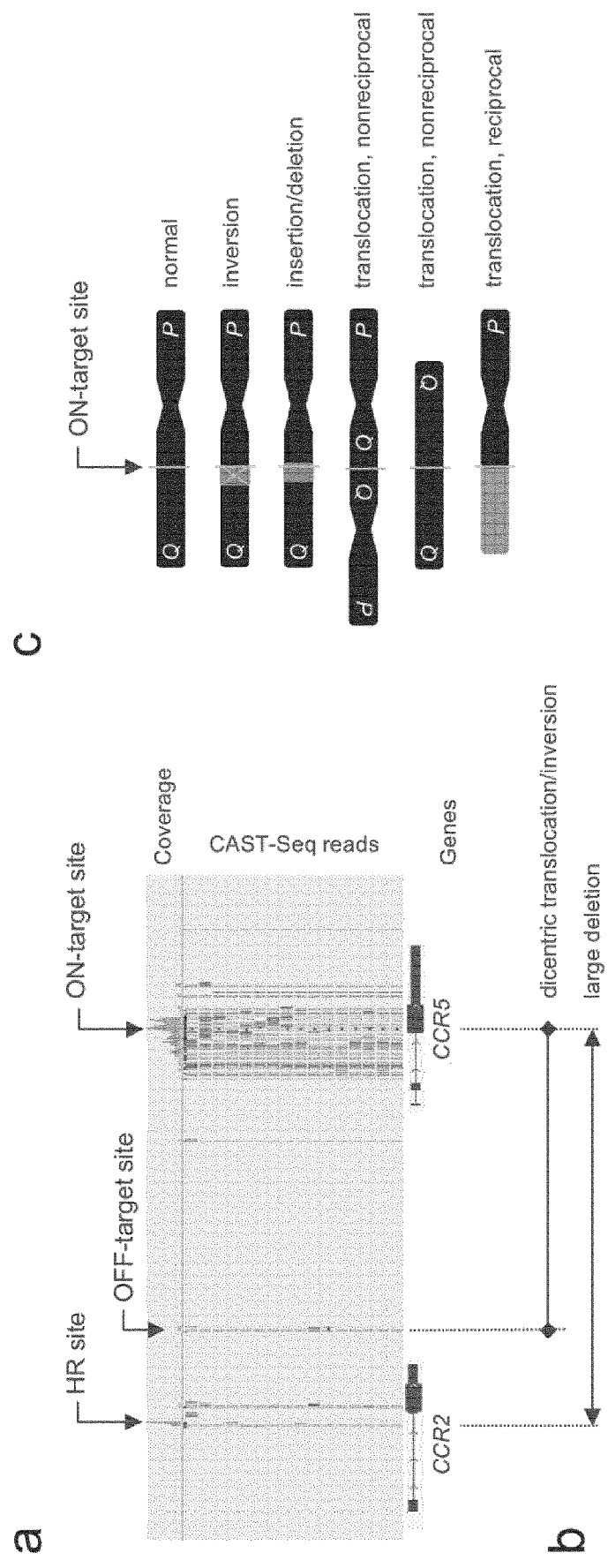
Figure 6. Schematic representation of CAST-Seq readouts at CCR2–CCR5 locus Figure 8
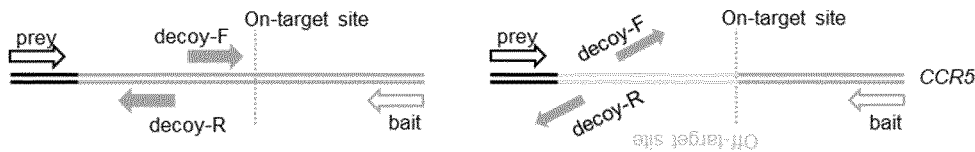
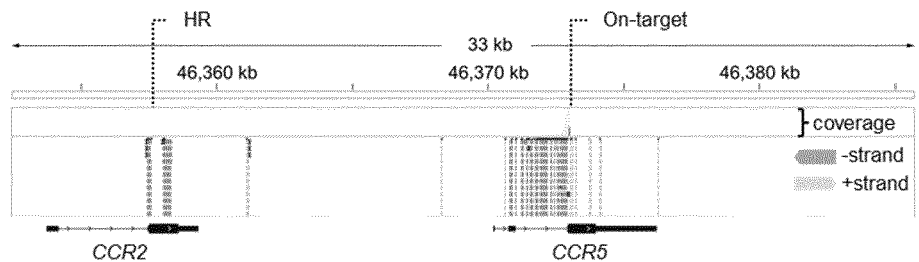
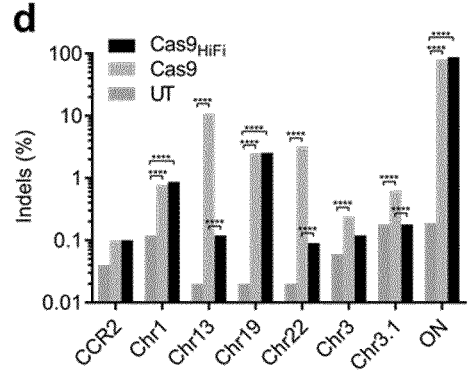
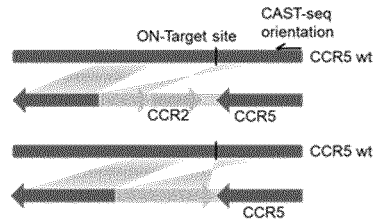
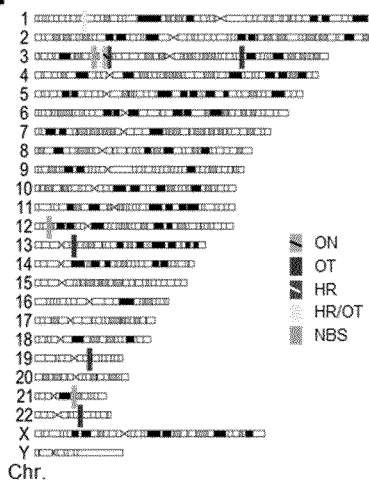
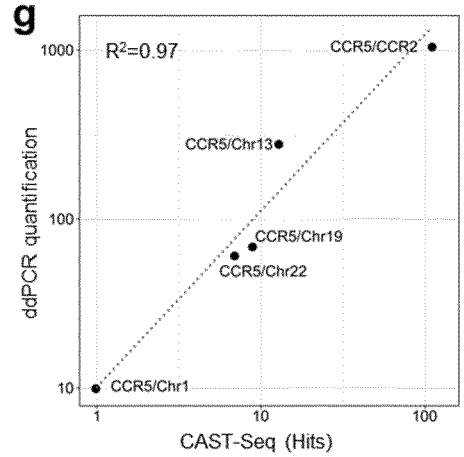

SEQUENCE LISTING

<160> NUMBER OF SEQ ID NOS: 64

<210> SEQ ID NO 1
<211> LENGTH: 23
<212> TYPE: DNA
<213> ORGANISM: artificial sequence
<220> FEATURE:
<223> OTHER INFORMATION: CCR5 Target

<400> SEQUENCE: 1
gtgagtagag cggaggcagg agg          23

<210> SEQ ID NO 2
<211> LENGTH: 23
<212> TYPE: DNA
<213> ORGANISM: artificial sequence
<220> FEATURE:
<223> OTHER INFORMATION: reference target
<220> FEATURE:
<221> NAME/KEY: misc_feature
<222> LOCATION: (21)..(21)
<223> OTHER INFORMATION: n is a, c, g, t or u

<400> SEQUENCE: 2
gtgagtagag cggaggcagg nrg          23

<210> SEQ ID NO 3
<211> LENGTH: 23
<212> TYPE: DNA
<213> ORGANISM: artificial sequence
<220> FEATURE:
<223> OTHER INFORMATION: VEGFA target

<400> SEQUENCE: 3
ggtgagtgag tgtgtgcgtg tgg          23

<210> SEQ ID NO 4
<211> LENGTH: 23

```
<212> TYPE: DNA
<213> ORGANISM: artificial sequence
<220> FEATURE:
<223> OTHER INFORMATION: FANCF target

<400> SEQUENCE: 4
ggaatccctt ctgcagcacc tgg                                          23

<210> SEQ ID NO 5
<211> LENGTH: 37
<212> TYPE: DNA
<213> ORGANISM: artificial sequence
<220> FEATURE:
<223> OTHER INFORMATION: linker positive strand

<400> SEQUENCE: 5
gtaatacgac tcactatagg gctccgctta agggact                           37

<210> SEQ ID NO 6
<211> LENGTH: 16
<212> TYPE: DNA
<213> ORGANISM: artificial sequence
<220> FEATURE:
<223> OTHER INFORMATION: linker negative strand

<400> SEQUENCE: 6
gtcccttaag cggagc                                                  16

<210> SEQ ID NO 7
<211> LENGTH: 22
<212> TYPE: DNA
<213> ORGANISM: artificial sequence
<220> FEATURE:
<223> OTHER INFORMATION: linker

<400> SEQUENCE: 7
gtaatacgac tcactatagg gc                                           22

<210> SEQ ID NO 8
<211> LENGTH: 59
<212> TYPE: DNA
<213> ORGANISM: artificial sequence
<220> FEATURE:
<223> OTHER INFORMATION: linker

<400> SEQUENCE: 8
acactctaca ctctttccct acacgacgct cttccgatct agggctccgc ttaagggac   59

<210> SEQ ID NO 9
<211> LENGTH: 20
<212> TYPE: DNA
<213> ORGANISM: artificial sequence
<220> FEATURE:
<223> OTHER INFORMATION: on target

<400> SEQUENCE: 9
aggtagatgt cagtcatgct                                              20

<210> SEQ ID NO 10
<211> LENGTH: 21
<212> TYPE: DNA
<213> ORGANISM: artificial sequence
<220> FEATURE:
<223> OTHER INFORMATION: decoy fwd

<400> SEQUENCE: 10
```

-continued atcaatgtga agcaaatcgc a                                    21

<210> SEQ ID NO 11
<211> LENGTH: 21
<212> TYPE: DNA
<213> ORGANISM: artificial sequence
<220> FEATURE:
<223> OTHER INFORMATION: decoy rev

<400> SEQUENCE: 11
atcaatgtga agcaaatcgc a                                    21

<210> SEQ ID NO 12
<211> LENGTH: 59
<212> TYPE: DNA
<213> ORGANISM: artificial sequence
<220> FEATURE:
<223> OTHER INFORMATION: on target nested

<400> SEQUENCE: 12
gactggagtt cagacgtgtg ctcttccgat ctgctcttca gccttttgca gtttatcag     59

<210> SEQ ID NO 13
<211> LENGTH: 21
<212> TYPE: DNA
<213> ORGANISM: artificial sequence
<220> FEATURE:
<223> OTHER INFORMATION: on target

<400> SEQUENCE: 13
ggattatcaa gtgtcaagtc c                                    21

<210> SEQ ID NO 14
<211> LENGTH: 18
<212> TYPE: DNA
<213> ORGANISM: artificial sequence
<220> FEATURE:
<223> OTHER INFORMATION: decoy fwd

<400> SEQUENCE: 14
ctggtcatcc tcatcctg                                        18

<210> SEQ ID NO 15
<211> LENGTH: 22
<212> TYPE: DNA
<213> ORGANISM: artificial sequence
<220> FEATURE:
<223> OTHER INFORMATION: decoy rev

<400> SEQUENCE: 15
aaaaccaaag atgaacacca gt                                   22

<210> SEQ ID NO 16
<211> LENGTH: 51
<212> TYPE: DNA
<213> ORGANISM: artificial sequence
<220> FEATURE:
<223> OTHER INFORMATION: on target nested

<400> SEQUENCE: 16
gactggagtt cagacgtgtg ctcttccgat ctatacatcg gagccctgcc a            51

<210> SEQ ID NO 17
<211> LENGTH: 18
<212> TYPE: DNA
<213> ORGANISM: artificial sequence

```
<220> FEATURE:
<223> OTHER INFORMATION: VEGFA on target

<400> SEQUENCE: 17
gagagggaca cacagatc                                                   18

<210> SEQ ID NO 18
<211> LENGTH: 19
<212> TYPE: DNA
<213> ORGANISM: artificial sequence
<220> FEATURE:
<223> OTHER INFORMATION: decoy fwd

<400> SEQUENCE: 18
cgtcttcgag agtgaggac                                                  19

<210> SEQ ID NO 19
<211> LENGTH: 17
<212> TYPE: DNA
<213> ORGANISM: artificial sequence
<220> FEATURE:
<223> OTHER INFORMATION: decoy rev

<400> SEQUENCE: 19
ctgctcgctc cattcac                                                    17

<210> SEQ ID NO 20
<211> LENGTH: 59
<212> TYPE: DNA
<213> ORGANISM: artificial sequence
<220> FEATURE:
<223> OTHER INFORMATION: on target nested

<400> SEQUENCE: 20
gactggagtt cagacgtgtg ctcttccgat ctacacagat ctattggaat cctggagtg      59

<210> SEQ ID NO 21
<211> LENGTH: 18
<212> TYPE: DNA
<213> ORGANISM: artificial sequence
<220> FEATURE:
<223> OTHER INFORMATION: FANCF on target

<400> SEQUENCE: 21
gttccaatca gtacgcag                                                   18

<210> SEQ ID NO 22
<211> LENGTH: 17
<212> TYPE: DNA
<213> ORGANISM: artificial sequence
<220> FEATURE:
<223> OTHER INFORMATION: decoy fwd

<400> SEQUENCE: 22
cttgagaccg ccagaag                                                    17

<210> SEQ ID NO 23
<211> LENGTH: 18
<212> TYPE: DNA
<213> ORGANISM: artificial sequence
<220> FEATURE:
<223> OTHER INFORMATION: decoy rev

<400> SEQUENCE: 23
cactacctac gtcagcac                                                   18
```

<210> SEQ ID NO 24
<211> LENGTH: 52
<212> TYPE: DNA
<213> ORGANISM: artificial sequence
<220> FEATURE:
<223> OTHER INFORMATION: on target nested

<400> SEQUENCE: 24
gactggagtt cagacgtgtg ctcttccgat ctgccgtctc caaggtgaaa gc      52

<210> SEQ ID NO 25
<211> LENGTH: 19
<212> TYPE: DNA
<213> ORGANISM: artificial sequence
<220> FEATURE:
<223> OTHER INFORMATION: Talen target

<400> SEQUENCE: 25
tgataggcac tgactctct                                            19

<210> SEQ ID NO 26
<211> LENGTH: 19
<212> TYPE: DNA
<213> ORGANISM: artificial sequence
<220> FEATURE:
<223> OTHER INFORMATION: right subunit

<400> SEQUENCE: 26
taagggtggg aaaatagac                                            19

<210> SEQ ID NO 27
<211> LENGTH: 22
<212> TYPE: DNA
<213> ORGANISM: artificial sequence
<220> FEATURE:
<223> OTHER INFORMATION: bait

<400> SEQUENCE: 27
gttggtatca aggttacaag ac                                        22

<210> SEQ ID NO 28
<211> LENGTH: 16
<212> TYPE: DNA
<213> ORGANISM: artificial sequence
<220> FEATURE:
<223> OTHER INFORMATION: decoy

<400> SEQUENCE: 28
ctgctggtgg tctacc                                               16

<210> SEQ ID NO 29
<211> LENGTH: 56
<212> TYPE: DNA
<213> ORGANISM: artificial sequence
<220> FEATURE:
<223> OTHER INFORMATION: bait nested

<400> SEQUENCE: 29
gactggagtt cagacgtgtg ctcttccgat ctgaccaata gaaactgggc atgtgg   56

<210> SEQ ID NO 30
<211> LENGTH: 23
<212> TYPE: DNA
<213> ORGANISM: artificial sequence
<220> FEATURE:
<223> OTHER INFORMATION: target

```
<400> SEQUENCE: 30
caatgtgtca actcttgaca ggg                                          23

<210> SEQ ID NO 31
<211> LENGTH: 18
<212> TYPE: DNA
<213> ORGANISM: artificial sequence
<220> FEATURE:
<223> OTHER INFORMATION: bait

<400> SEQUENCE: 31
aaacacagca tggacgac                                                18

<210> SEQ ID NO 32
<211> LENGTH: 21
<212> TYPE: DNA
<213> ORGANISM: artificial sequence
<220> FEATURE:
<223> OTHER INFORMATION: decoy

<400> SEQUENCE: 32
ccagtgggac tttggaaata c                                            21

<210> SEQ ID NO 33
<211> LENGTH: 18
<212> TYPE: DNA
<213> ORGANISM: artificial sequence
<220> FEATURE:
<223> OTHER INFORMATION: decoy rev

<400> SEQUENCE: 33
gcatagtgag cccagaag                                                18

<210> SEQ ID NO 34
<211> LENGTH: 59
<212> TYPE: DNA
<213> ORGANISM: artificial sequence
<220> FEATURE:
<223> OTHER INFORMATION: bait nested

<400> SEQUENCE: 34
gactggagtt cagacgtgtg ctcttccgat ctaggaggat gatgaagaag attccagag   59

<210> SEQ ID NO 35
<211> LENGTH: 25
<212> TYPE: DNA
<213> ORGANISM: artificial sequence
<220> FEATURE:
<223> OTHER INFORMATION: forw

<400> SEQUENCE: 35
ttattataca tcggagccct gccaa                                        25

<210> SEQ ID NO 36
<211> LENGTH: 28
<212> TYPE: DNA
<213> ORGANISM: artificial sequence
<220> FEATURE:
<223> OTHER INFORMATION: rev

<400> SEQUENCE: 36
tgctcttcag ccttttgcag tttatcag                                     28

<210> SEQ ID NO 37
```

<210> SEQ ID NO 37
<211> LENGTH: 23
<212> TYPE: DNA
<213> ORGANISM: artificial sequence
<220> FEATURE:
<223> OTHER INFORMATION: ccr5 forw

<400> SEQUENCE: 37
agtttgcatt catggagggc aac                                                23

<210> SEQ ID NO 38
<211> LENGTH: 26
<212> TYPE: DNA
<213> ORGANISM: artificial sequence
<220> FEATURE:
<223> OTHER INFORMATION: ccr5 rev

<400> SEQUENCE: 38
ggcagggctc cgatgtataa taattg                                             26

<210> SEQ ID NO 39
<211> LENGTH: 22
<212> TYPE: DNA
<213> ORGANISM: artificial sequence
<220> FEATURE:
<223> OTHER INFORMATION: ccr5 forw

<400> SEQUENCE: 39
catgctggtc atcctcatcc tg                                                 22

<210> SEQ ID NO 40
<211> LENGTH: 23
<212> TYPE: DNA
<213> ORGANISM: artificial sequence
<220> FEATURE:
<223> OTHER INFORMATION: ccr5 rev

<400> SEQUENCE: 40
cccagaaggg gacagtaaga agg                                                23

<210> SEQ ID NO 41
<211> LENGTH: 23
<212> TYPE: DNA
<213> ORGANISM: artificial sequence
<220> FEATURE:
<223> OTHER INFORMATION: edge forw

<400> SEQUENCE: 41
tccttcttac tgtccccttc tgg                                                23

<210> SEQ ID NO 42
<211> LENGTH: 21
<212> TYPE: DNA
<213> ORGANISM: artificial sequence
<220> FEATURE:
<223> OTHER INFORMATION: edge rev

<400> SEQUENCE: 42
agcaaacaca gcatggacga c                                                  21

<210> SEQ ID NO 43
<211> LENGTH: 22
<212> TYPE: DNA
<213> ORGANISM: artificial sequence
<220> FEATURE:
<223> OTHER INFORMATION: ccr5 forw

<400> SEQUENCE: 43
catgctggtc atcctcatcc tg                                              22

<210> SEQ ID NO 44
<211> LENGTH: 23
<212> TYPE: DNA
<213> ORGANISM: artificial sequence
<220> FEATURE:
<223> OTHER INFORMATION: ccr5 rev

<400> SEQUENCE: 44
cccagaaggg gacagtaaga agg                                             23

<210> SEQ ID NO 45
<211> LENGTH: 22
<212> TYPE: DNA
<213> ORGANISM: artificial sequence
<220> FEATURE:
<223> OTHER INFORMATION: ccr5 forw

<400> SEQUENCE: 45
atcgataggt acctggctgt cg                                              22

<210> SEQ ID NO 46
<211> LENGTH: 25
<212> TYPE: DNA
<213> ORGANISM: artificial sequence
<220> FEATURE:
<223> OTHER INFORMATION: ccr5 rev

<400> SEQUENCE: 46
gtatggaaaa tgagagctgc aggtg                                           25

<210> SEQ ID NO 47
<211> LENGTH: 23
<212> TYPE: DNA
<213> ORGANISM: artificial sequence
<220> FEATURE:
<223> OTHER INFORMATION: ccr5 telomere forw

<400> SEQUENCE: 47
tgccaaggca tcttacctct tcc                                             23

<210> SEQ ID NO 48
<211> LENGTH: 24
<212> TYPE: DNA
<213> ORGANISM: artificial sequence
<220> FEATURE:
<223> OTHER INFORMATION: ccr5 telomere rev

<400> SEQUENCE: 48
gcatctggtc ttctgctaca ctgg                                            24

<210> SEQ ID NO 49
<211> LENGTH: 23
<212> TYPE: DNA
<213> ORGANISM: artificial sequence
<220> FEATURE:
<223> OTHER INFORMATION: ccr5 mylk forw

<400> SEQUENCE: 49
cagccttgtg attcatgctg tcc                                             23

<210> SEQ ID NO 50
<211> LENGTH: 25
<212> TYPE: DNA

```
<213> ORGANISM: artificial sequence
<220> FEATURE:
<223> OTHER INFORMATION: ccr5 mylk rev

<400> SEQUENCE: 50
ggactcacct tctactgtca actcc                                          25

<210> SEQ ID NO 51
<211> LENGTH: 25
<212> TYPE: DNA
<213> ORGANISM: artificial sequence
<220> FEATURE:
<223> OTHER INFORMATION: hbb edge forw

<400> SEQUENCE: 51
agaccaatag aaactgggca tgtgg                                          25

<210> SEQ ID NO 52
<211> LENGTH: 22
<212> TYPE: DNA
<213> ORGANISM: artificial sequence
<220> FEATURE:
<223> OTHER INFORMATION: hbb edge rev

<400> SEQUENCE: 52
atcactaaag gcaccgagca ct                                             22

<210> SEQ ID NO 53
<211> LENGTH: 22
<212> TYPE: DNA
<213> ORGANISM: artificial sequence
<220> FEATURE:
<223> OTHER INFORMATION: HBB forw

<400> SEQUENCE: 53
ggctcatggc aagaaagtgc tc                                             22

<210> SEQ ID NO 54
<211> LENGTH: 21
<212> TYPE: DNA
<213> ORGANISM: artificial sequence
<220> FEATURE:
<223> OTHER INFORMATION: hbb rev

<400> SEQUENCE: 54
cagtgcagct cactcagtgt g                                              21

<210> SEQ ID NO 55
<211> LENGTH: 22
<212> TYPE: DNA
<213> ORGANISM: artificial sequence
<220> FEATURE:
<223> OTHER INFORMATION: hbb rev

<400> SEQUENCE: 55
ctgaggagaa gtctgccgtt ac                                             22

<210> SEQ ID NO 56
<211> LENGTH: 23
<212> TYPE: DNA
<213> ORGANISM: artificial sequence
<220> FEATURE:
<223> OTHER INFORMATION: hbb rev

<400> SEQUENCE: 56
ccacatgccc agtttctatt ggt                                            23
```

<210> SEQ ID NO 57
<211> LENGTH: 21
<212> TYPE: DNA
<213> ORGANISM: artificial sequence
<220> FEATURE:
<223> OTHER INFORMATION: hbb telomere forw

<400> SEQUENCE: 57
gggccaggga agtgtatgat g                                              21

<210> SEQ ID NO 58
<211> LENGTH: 21
<212> TYPE: DNA
<213> ORGANISM: artificial sequence
<220> FEATURE:
<223> OTHER INFORMATION: hbb telomer rev

<400> SEQUENCE: 58
acagacatca gtgccattgc g                                              21

<210> SEQ ID NO 59
<211> LENGTH: 20
<212> TYPE: DNA
<213> ORGANISM: artificial sequence
<220> FEATURE:
<223> OTHER INFORMATION: hbb pod1 forw

<400> SEQUENCE: 59
gcaggttcag tccctcttgg                                                20

<210> SEQ ID NO 60
<211> LENGTH: 21
<212> TYPE: DNA
<213> ORGANISM: artificial sequence
<220> FEATURE:
<223> OTHER INFORMATION: hbb pod1 rev

<400> SEQUENCE: 60
tgcttggcct atggacagtt g                                              21

<210> SEQ ID NO 61
<211> LENGTH: 20
<212> TYPE: DNA
<213> ORGANISM: artificial sequence
<220> FEATURE:
<223> OTHER INFORMATION: common target rad forw

<400> SEQUENCE: 61
ccttcagctc tgtggtgacg                                                20

<210> SEQ ID NO 62
<211> LENGTH: 21
<212> TYPE: DNA
<213> ORGANISM: artificial sequence
<220> FEATURE:
<223> OTHER INFORMATION: common target rad rev

<400> SEQUENCE: 62
cccttctcag caaagtccct g                                              21

<210> SEQ ID NO 63
<211> LENGTH: 19
<212> TYPE: DNA
<213> ORGANISM: artificial sequence
<220> FEATURE:

```
<223> OTHER INFORMATION: common target stat forw

<400> SEQUENCE: 63
actctcacgg acgaggagc                                                    19

<210> SEQ ID NO 64
<211> LENGTH: 24
<212> TYPE: DNA
<213> ORGANISM: artificial sequence
<220> FEATURE:
<223> OTHER INFORMATION: common target stat rev

<400> SEQUENCE: 64
cagttttcta gccgatctag gcag                                              24
```

METHOD FOR CHARACTERIZATION OF MODIFICATIONS CAUSED BY THE USE OF DESIGNER NUCLEASES

PRIORITY

This application corresponds to the U.S. National Phase of International Application No. PCT/EP2019/075101, filed Sep. 19, 2018, which, in turn, claims priority to European Patent Application No. 18196438.8 filed Sep. 25, 2018, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Mar. 17, 2021, is named LNK_226 US_SEQ_LIST.txt and is 12,232 bytes in size.

BACKGROUND OF THE INVENTION

Genome editing describes the targeted modification of the genomes of any kind of cell type of interest with so-called "designer nucleases".

Several designer nucleases are known, which are also designated as "programmable nucleases" or "engineered nucleases". Examples thereof are zinc-finger nuclease (ZFNs), transcriptional activator-like effector nucleases (TALENs) and RNA-guided engineered nucleases (RGENs) which may be derived from the clustered regularly interspaced repeat (CRISPR/Cas) prokaryotic adaptive immunity system. Such means are important and widely used for genome editing not only in cultured cells but also in whole organisms. Designer nucleases have an origin in nature but are artificially modified in order to act in an intended manner.

Genome editing has broad applications and has been successfully employed to genetically modify prokaryotic and eukaryotic microorganisms, crops, livestock, model organisms for research, cell lines for drug screening, and various cell types or organs for therapeutic applications. For most of these applications, the specificity of the employed designer nuclease is a key parameter to ensure maintenance of genome integrity of the edited cell type.

In the context of clinical applications in humans, relevant cell types that have been edited with designer nucleases include hematopoietic stem cells, B and T cells, epidermal stem cells, pluripotent stem cells, liver cells, muscle cells, and retinal cells. Relevant disease targets include (but are not limited to) hereditary disorders, in particular hereditary disorders with dominant inheritance or diseases caused by mutations in tightly regulated genes, infectious diseases, or cancer.

Before employing genome editing in transplantable cell types ex vivo or before applying gene editing tools in vivo directly in the patient, the designer nucleases need to be carefully evaluated with respect to activity and specificity. Specificity of engineered endonucleases is the key for any clinical translation of gene editing in order to maintain genome integrity and to reduce the risk of inducing oncogenic mutations. The consequence of designer nuclease induced mutagenesis at so-called off-target sites and/or the resulting chromosomal aberrations are often referred to as genotoxicity that eventually could lead to cancer.

The term "on-target site" is used in the present application to designate a site at which a DNA double strand break is intended to be introduced by using "designer nucleases". Such intended site of action is usually designated as "on-target site".

The designer nucleases have a certain sequence specificity and thus work at such "on-target site". The designer nucleases may, however, also work at so-called "off-target sites" which show a certain degree of sequence homology to the "on-target site". The term "off-target site" as used herein refers to a site where the designer nucleases have activity and which usually have a sequence that is not identical to the target sequence of the designer sequence. An "off-target site" relates to a sequence other than an "on-target site" that is cleaved by the designer nucleases. The fact that designer nucleases have an activity even at sites different from the on-target site may be due to phenomena that can be caused by various reasons. The downside of designer nucleases cleaving at off-target sites is that this can result in undesired side effects like mutations, deletions, sequence inversions and other disturbances in the genome which should be avoided.

In general, designer nuclease induced off-target activity can lead to short insertion/deletion (indel) mutations, large chromosomal deletions, chromosomal inversions, as well as chromosomal translocations. On the molecular level, off-target activity occurs when the DNA binding moieties of designer nucleases bind to sequences in the genome that share homology to the actual target site. Much effort has been invested in increasing the safety of genome-editing tools in the past decade, leading to better designer nucleases with much higher specificity.

Nonetheless, a thorough preclinical assessment of designer nuclease specificity is a clearly stated requirement by the regulatory bodies, such as the Paul Ehrlich Institute in Germany or the U.S. Food and Drug Administration (FDA). There is a need for applied diagnostic methods which are highly sensitive and allow skilled persons not only to measure off-target mutagenesis but also chromosomal aberrations and/or any other unexpected genomic modifications with high sensitivity.

To assess the genotoxic risk associated with the application of designer nucleases such as CRISPR-Cas nucleases, several methods have been developed to determine either off-target activity of designer nucleases or designer nuclease induced chromosomal aberrations. In principle, these methods can be subdivided into computer-based prediction algorithms (in silico methods), in vitro test methods and cell-based methods. All of these methods rely on next generation sequencing (NGS) and are typically employed in a two-step process: A 'screening assay' is first used to identify all potentially possible off-target sites in the genome of interest. A subsequent 'confirmatory assay' is used to sequence the potential off-target sites defined in the screening test in the genome of the gene edited cells.

In silico prediction algorithms are based on well-defined parameters, including similarity to the target sequence (Lee et al. (2016), Mol Ther 24, 475-487). They represent a fast and relatively cheap 'screening assay', but more often than not, those algorithms miss critical off-target sites. In contrast to the in silico analysis, experimental methods allow for the identification of off-targets independently of predetermined parameters and are consequently less biased. However, experimental methods are more laborious and more expensive. In addition, they are subject to technical limitations and some of them lack sensitivity.

At present, several experimental 'screening assays' are employed to determine off-target sites and are likely sensitive enough to be considered for preclinical evaluation of designer nuclease specificity, like for example:

a) EP 3 219 810 (whole genome sequencing)
b) Guide-Seq (Tsai et al. (2015), Nat Biotechnol 33, 187-197),
c) BLISS (Yan et al. (2017), Nat Commun 8, 15058),
d) Digenome-Seq (Kim et al. (2015), Nat Methods 12, 237-243), and
e) Circle-Seq (Tsai et al. (2017), Nat Methods 14, 607-614).

Guide-Seq is a cell-based method that introduces short double-stranded oligodeoxynucleotides (dsODN) into the cell in addition to the designer nuclease. Once the designer nuclease cuts the genome, the short dsODN is integrated by the cellular DNA repair machinery into the resulting DNA double-strand breaks, and can then serve as a starting point for high-throughput sequencing. This method works well but only in certain human cell lines whose genome can differ considerably from the genome of the patient.

BLISS detects actual DNA double strand breaks in cells by means of an in vitro oligo ligation to the available DNA ends. The ligated DNA is in vitro transcribed and the library sequenced by high-throughput sequencing. Digenome-Seq and Circle-Seq are in vitro methods, which are based on the cleavage of the whole genome or circularized genome fragments with CRISPR-Cas.

For Digenome-Seq, whole-genome sequencing is performed on the in vitro cleaved genomes, which will yield sequence reads with the same 5' ends at cleavage sites that can then be computationally identified. To reach the necessary coverage and therefore sufficient sensitivity, Digenome-Seq must be performed on high-throughput sequencing machines, such as the Illumine HiSeq line. In consequence, the application of Digenome-Seq is rather expensive.

In Circle-Seq sequencing adapters are ligated to the cleaved 5' ends, which then can be used for NGS to identify the off-target sites. However, Circle-Seq may suffer from potential biases resulting from the need to circularize genomic DNA and requires large amounts of input DNA.

Hence, Circle-Seq cannot be performed if only limited amount of sample, e.g. a biopsy, is available. In all cases, these experimentally determined off-target sites must be validated in the patient's cells using NGS-based 'confirmatory assays', such as multiplexed targeted amplicon sequencing, to establish an actual specificity profile of the nucleases in the clinically relevant target cells.

Importantly, the above-described methods allow researchers to predict off-target sites which are cleaved by the designer nuclease of choice, but none of them enable an assessment of gross chromosomal aberrations induced by programmable nucleases, such as recently described (Kosicki et al. (2018), Nat Biotechnol 36, 765-771).

Two further described methods, high-throughput genome-wide translocation sequencing (HTGTS) and uni-directional targeted sequencing methodology (UDiTaS) can identify translocations or other chromosomal aberrations induced by designer nucleases. HTGTS (WO 2016/081798) and UDiTaS (WO 2018/129368) disclose methods relating to the detection of non-specific DNA double-strand breaks in the genome. These two methods also allowed for the identification of translocation events but the described bioinformatic analyses as well as the biased genomic fragmentation (use of Tn5 tagmentation for UDiTaS, restriction enzymes for HTGTS) considerably limit sensitivity of these approaches. HTGTS does neither state a lower limit of detection (LLoD) nor sensitivity. UDiTaS's LLoD is indicated as 0.1%.

All known methods cannot identify chromosomal rearrangements that are not related to off-target activity of a designer nuclease. In particular, these methods cannot identify homology-mediated chromosomal rearrangements that are triggered by on-target activity of a designer nuclease.

HTGTS and UDiTaS are not quantitative with regard to unknown translocation events.

HTGTS and UDiTaS were not shown to work on genomic DNA harvested from a gene-edited, clinically relevant cell type, i.e. hematopoietic stem cells.

SUMMARY OF THE INVENTION

It is an object of the present invention to provide a method that can identify genomic modifications, including gross chromosomal aberrations, and that is (i) highly sensitive, (ii) highly specific, (iii) quantitative, (iv) able to detect previously undescribed types of chromosomal rearrangements, and (v) performed directly on genomic DNA isolated from the clinically relevant cell type. The method is designated herein as CAST-Seq (chromosomal aberration analysis by single targeted linker-mediated PCR).

CAST-Seq is based on single targeted linker-mediated PCR (LM-PCR) and uses decoy primers to enhance the signal-to-noise ratio. This method allows to identify off-target sites and to detect genomic modifications derived from both on- and off-target activity of designer nucleases, including large deletions, inversions and translocations with unmatched sensitivity. Importantly, because CAST-Seq's high sensitivity, the assay can be performed with less than 1 µg of genomic DNA as input. CAST-Seq can therefore be applied directly to any clinically relevant human cell type of choice, including ex vivo gene edited cells before transplantation or cells derived from a biopsy of gene edited organs. This unique setup and the fact that CAST-Seq is performed directly in the gene edited cell type or tissue of interest, CAST-Seq may make an NGS-based confirmation assay redundant by straightforwardly uniting the 'screening test' with the 'confirmatory test'. CAST-Seq may therefore substantially improve the process by detecting chromosomal aberrations at "on-target sites" and "off-target-sites".

BRIEF DESCRIPTION OF THE DRAWINGS

The preferred embodiments of the present invention are further described and illustrated in the figures and examples of the present application.

The following abbreviations were used in the Figures and Tables as well as in the experiments:

Figure 7:
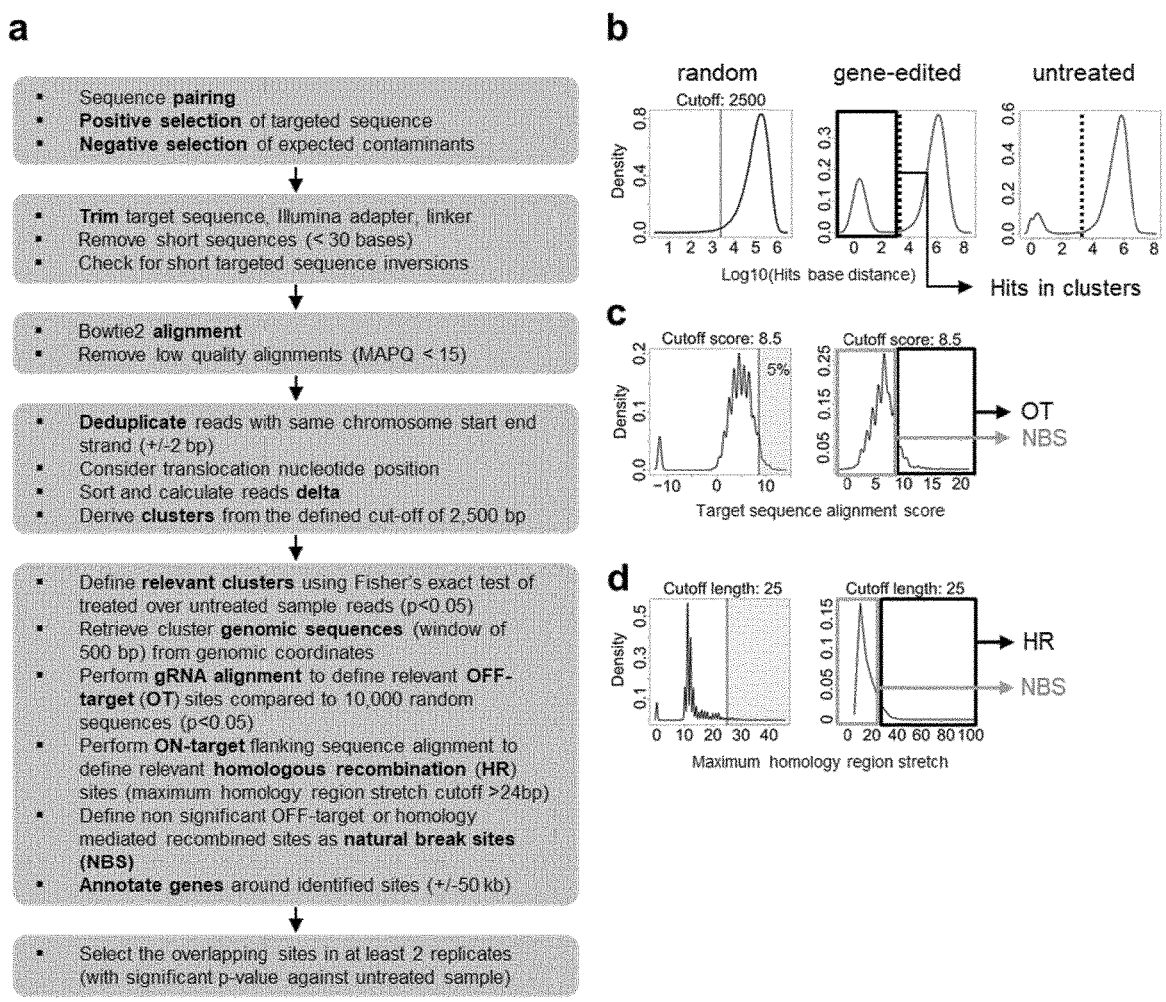

| Abbreviation | Explanation |
| --- | --- |
| CBS | Common breaking site |
| CCR2 | C-C chemokine receptor type 2 |
| CCR5 | C-C chemokine receptor type 5 |
| CD34 | Cluster of differentiation 34 |
| ddPCR | Droplet digital PCR |
| DSB | DNA double strand break |
| FASTQ | Fast alignment search tool quality file format |
| FANCF | Fanconi anemia complementation group F |
| FLASh | Fast length adjustment of short reads |
| HTGTS | High-throughput genome-wide translocation sequencing |
| HR | Homologous recombination |
| IGV | Integrative genome viewer |
| LM-PCR | Linker-mediated PCR |

-continued

| Abbreviation | Explanation |
|---|---|
| NBS | Naturally occurring breaking site |
| NGS | Next generation sequencing |
| OT | Off-target site |
| PAM | Protospacer adjacent motif |
| PCR | Polymerase chain reaction |
| SAMtools | Sequence alignment/map tools |
| UDiTaS | Uni-directional targeted sequencing methodology |
| VEGFA | Vascular endothelial growth factor A |

In particular, the Figures show the results of the experiments as follows:

FIG. 1. Schematic of CAST-Seq pipeline.

(a) Library preparation. Simultaneous ON-target (dark grey chromosome) and OFF-target (light grey chromosome) activity of designer nucleases (illustrated by scissor) in cells can induce a translocation between the two DNA double strand breaks (DSBs), leading e.g. to a reciprocal translocation. The target chromosome is thereby separated into a centromeric (c) part and a telomeric (t) part. In most cases, no translocation will happen (right side). Genomic DNA derived from untreated and gene edited cells is randomly fragmented and end-repaired to allow for the addition of a 3'-A overhang. This short overhang is used for subsequent ligation of a short linker (black). For simplification, only the reaction with the centromeric end is depicted. A second reaction with the telomeric end (very left) is performed analogously. The $1^{st}$ PCR is performed with primers (open arrows) binding to the target site and the linker sequences. So-called 'decoy' primers (filled arrows), which are designed to bind in close proximity to the on-target cleavage site, are added to the PCR reaction. They cannot bind to translocation events (left) but prevent the amplification of non-modified target sites (right) by generating short amplicons that cannot be further amplified in the next PCR steps. The $2^{nd}$ PCR is performed with nested primers harboring 5'-overhangs that are utilized in the $3^{rd}$ PCR step to add the barcodes for NGS. (b) Bioinformatics pipeline. FASTQ files derived from NGS are processed according to the schematic overview. The boxes group the main steps in the bioinformatics flow: pairing and filtering, trimming, alignment, cluster definition, and cluster analysis.

FIG. 2. Bioinformatical definition of categories.

(a) Read base distance. In order to calculate the likelihood of a read to fall into a cluster by chance, rather than a designer nuclease provoked event, the CAST-Seq sample from gene edited cells was compared to an in silico created random read library that contains the same number of reads. The distribution of the distance of consecutive reads is shown on a logarithmic scale. In this example, the 2,500-bp threshold line describes an area of <5% in the random library, meaning that the likelihood of a read to fall into one cluster by chance is smaller than 5% ($p<0.05$). CAST-Seq analysis from untreated cells is shown as a control. (b) Target sequence alignment score. A 500-bp genomic region surrounding these translocation sites was compared against 10,000 random sequences of 500-bp. Every site was aligned to the designer nuclease target sequence using a scoring table (Table 12). If the target sequence alignment score of the sequence was higher than the 5% best score in the random sequences, the event was classified as OFF-target (OT) activity derived translocation. (c) Maximum homology region stretch. For non-OT sites, the longest common homologous substring between the target region and the translocation region was searched within a 5 kb window surrounding the translocation site. If the homologous substring length was higher than the 5% longest substring in the random sequences, the event was classified as homologous recombination (HR)-mediated translocation. All other were categorized as common breaking site (CBS)-derived translocation.

FIG. 3. Effect of decoy oligonucleotide primers (a) Schematic of decoy test system. Efficacy of decoy primers (filled arrows) was tested on the CCR5 locus using two locus-specific primers (open arrows) that amplify a fragment of 412 bp. The presence of the decoy primers should reduce or prevent the amplification of the 412 bp-fragment. F, forward primer; R, reverse primer. (b) Use of blocked decoy primers. PCR was performed with CCR5 primers in combination with decoy primers that are blocked by 3' phosphorylation (filled bars). The following amplifications are shown: Controls: F, reaction with only CCR5 forward primer; 1 D, only one of the two decoy primers was used; H$_2$O, no template in reaction. 1:1; 1:5 and 1:10 reflect the ratio of CCR5 ON-target primers to decoy primers. (c) Non-blocked decoy primers. PCR was performed with CCR5-specific primers in combination with non-blocked decoy primers. The following amplifications are shown: Control H$_2$O, no template in reaction. 1:1; 1:5 and 1:10 reflect the ratio of CCR5 ON-target primers to decoy primers. (d) Single non-blocked decoy primer. PCR was performed with CCR5 primers in combination with only reverse orientation decoy primer. The following amplifications are shown: Control F, CCR5 forward primer in combination with reverse decoy primer. (b-d) The sizes of the amplicons are indicated on the left, the different ratios of CCR5 to decoy primers that was tested is indicated on the bottom as 1:1, 1:5, 1:10. All primer sequences are indicated in Table 2.

As can be seen from FIG. 3, the non-blocked decoy primer could efficiently reduce or prevent the amplification of the 412 bp-fragment (c) and (d). This suggests that the use of decoy primers can shift the ratio of ON-target site amplification to amplification of PCR templates containing a translocation event (see FIG. 1a). Hence, in the first amplification round (see FIG. 1a), the non-blocked decoy primer(s) prevent or reduce substantially the amplification of non-translocation events whereas the use of blocked decoy primers does not have such effect (b).

FIG. 4. Genomic modifications mapped by CAST-seq.

Genomic DNA isolated from CD34-positive hematopoietic stem and progenitor cells, which were edited with CRISPR-Cas9 ribonucleoprotein complexes targeting exon 3 in the CCR5 locus (target site: 5'-GTGAGTAGAGCG-GAGGCAGGAGG (SEQ ID NO:1), PAM underlined), was subjected to CAST-Seq. (a) Mapping of genomic modifications. All relevant genomic modification sites identified by CAST-Seq are shown in a chromosome ideogram. The mapped sites can be subdivided in three main categories: chromosomal aberrations mediated by off-target (OT) sites, by homology mediated recombination (HR), or by common breaking sites (CBS). (b) OT analysis. The pie charts indicate the fractions of mismatches and bulges found in the mapped sites. The numbers of mismatches/bulges are indicated from 0 to 5 and more.

FIG. 5. Alignment.

Genomic DNA isolated from CD34-positive hematopoietic stem and progenitor cells, which were edited with CRISPR-Cas9 ribonucleoprotein complexes targeting exon 3 in the CCR5 locus (target site: 5'-GTGAGTAGAGCG-GAGGCAGGAGG (SEQ ID NO:1), PAM underlined), was subjected to CAST-Seq. (a) Alignment. The reference target site (top row: 5'-GTGAGTAGAGCGGAGGCAGGNRG (SEQ ID NO:2); PAM underlined; N, any nucleotide; R, purine) and the top 25 Off-target (OT) sites identified by CAST-Seq are indicated. Mismatched nucleotides and bulges, i.e. nucleotide insertions/deletions within the OFF-target sites with respect to the reference target site, are highlighted. "1" stands for 1 nucleotide insertion, "−1" for a 1 nucleotide deletion. Cluster start position is indicated on the left. (b) Off-target sequence diversity. A sequence logo was created from the collection of aligned off-target sites, depicting the consensus sequence and the diversity of the off-target sequences. (c) Tolerance to mismatches and bulges. The identified OFF-target sites were aligned to the 23 nucleotide-long target sequence and then grouped into 4 nucleotide-long regions recognized by the gRNA (1-4, 5-8, 9-12, 13-16, 17-20) and the 3 nucleotide-long stretch bound by the Cas9 protein (PAM, 21-23). Indicated is the fraction of mismatches and bulges that are found in each of these groups.

FIG. 6. Schematic representation of CAST-Seq readout.

CD34-positive hematopoietic stem and progenitor cells were edited with CRISPR-Cas9 ribonucleoprotein complexes that target the CCR5 locus in exon 3 (target site: 5'-GTGAGTAGAGCGGAGGCAGGAGG (SEQ ID NO:1), PAM underlined). Genomic DNA was extracted after 7 days and subjected to CAST-Seq. (a) Visualization of CAST-seq results. IGV was used to visualize CAST-Seq results in the neighborhood of the CCR5 target locus. Every mapped CAST-Seq read is represented by a bar. Light grey bars indicate reverse and dark grey bars forward orientation, respectively. Coverage, i.e. the number or mapped reads, is indicated on the top, the location of the CCR5 and the CCR2 loci on the bottom. (b) Examples of chromosomal aberrations. Two examples are indicated on how to interpret the results: (1) a dicentric translocation and sequence inversion induced by simultaneous ON-target activity at the CCR5 locus and OFF-target site activity in close proximity to CCR2; (2) a large deletion prompted by ON-target activity at the CCR5 locus that provoked a homologous recombination (HR) event with a site in the CCR2 locus that shares high sequence homology to the ON-target site in CCR5. (c) Schematic overview of all gross chromosomal aberration identified by CAST-Seq after cleavage at the ON-target site.

FIG. 7. More restrictive bioinformatics pipeline.

(a) Overview. FASTQ files derived from NGS were processed according to the overview. The boxes group the main steps in the bioinformatics flow: pairing and filtering, trimming, alignment, cluster definition, cluster analysis, filtering. (b) Read base distance. In order to calculate the likelihood of a read to fall into a cluster by chance rather than a designer nuclease provoked event, the CAST-Seq sample from gene edited cells was compared to an in silico created random read library that contains the same number of reads. The distribution of the distance of consecutive reads is shown on a logarithmic scale. In this example, the 2,500-bp threshold line describes an area of <5% in the random library, meaning that the likelihood of a read to fall into one cluster by chance is smaller than 5% ($p<0.05$). CAST-Seq analysis from untreated cells is shown as a control. (c) target sequence alignment score. A 500-bp genomic region surrounding these translocation sites was compared against 10,000 random sequences of 500-bp. Every site was aligned to the designer nuclease target sequence. If the target sequence alignment score of the site was higher than the 5% best score in the random sequences, the event was classified as off-target (OT) activity derived translocation. (d) Maximum homology region stretches. The longest common homologous substring between the target region and the translocation region was searched within a 5 kb window surrounding the translocation site. If the homologous substring length was longer than the 24 bp, the event was classified as homologous recombination (HR)-mediated translocation. All others were categorized as naturally occurring breaking site (NBS)-derived translocation.

FIG. 8. CAST-Seq analysis of CCR5[#1] targeting CRISPR-Cas9 nuclease with more restrictive bioinformatics algorithm.

(a) Schematic of decoy strategy. Prey and bait primers bind to linker and on-target site, respectively, to amplify chromosomal aberrations. Decoy primers bind in close proximity to on-target site but opposite to bait primer in order to prevent the formation of full-length amplicons at non-modified target sites (left). (b) Qualitative CAST-Seq analysis. Integrative Genomics Viewer (IGV) plots illustrate CAST-Seq reads surrounding the target region within a window of 33 kb. Every mapped CAST-Seq read is represented by a bar (only top 7 lines shown). Dark grey bars indicate sequences aligning to the negative strand and light grey bars to the positive strand. Coverage, i.e. the number of mapped reads, is indicated on the middle, gene locations on the bottom. Positions of on-target site and CCR2 HR cluster are emphasized by dotted lines. (c) Target site alignment. Reference CCR5[#1] target site is shown on top (N, any nucleotide; R, purine). Mismatched nucleotides and deletions/insertions (−1/1) are highlighted. Number of hits are listed on the left, categories on right. (d) Indel analysis. Targeted deep amplicon sequencing was performed on identified HR and/or OT sites of genomic DNA harvested 4 days after gene editing with Cas9 or HiFi-Cas9. Statistically significant differences are indicated by '*' ($p<0.05$; Z-test corrected by standard deviation calculated on untreated cells (UT)). (e) Graphical representation of selected complex rearrangements found at on-target site. E.g. a combination of inverted CCR2 (light grey) and CCR5 (dark grey) derived sequences (top) or a long stretch of an inverted/duplicated CCR5 sequence (dark grey, bottom). (f) Mapping of chromosomal rearrangements. All relevant chromosomal aberration sites identified by CAST-Seq are shown in a chromosome ideogram. The mapped sites are subdivided in the on-target site cluster (ON) as well as chromosomal rearrangements mediated by off-target cleavage (OT), by homology-mediated recombination (HR), or by naturally occurring break sites (NBS). Yellow bars indicate ambiguous categorization (HR/OT). (g) Quantification. The number of chromosomal rearrangements quantified by CAST-Seq or ddPCR are represented in scatter plot. Linear regression line (dotted) and squared correlation coefficient ($R^2$) are indicated.

Figure 9:
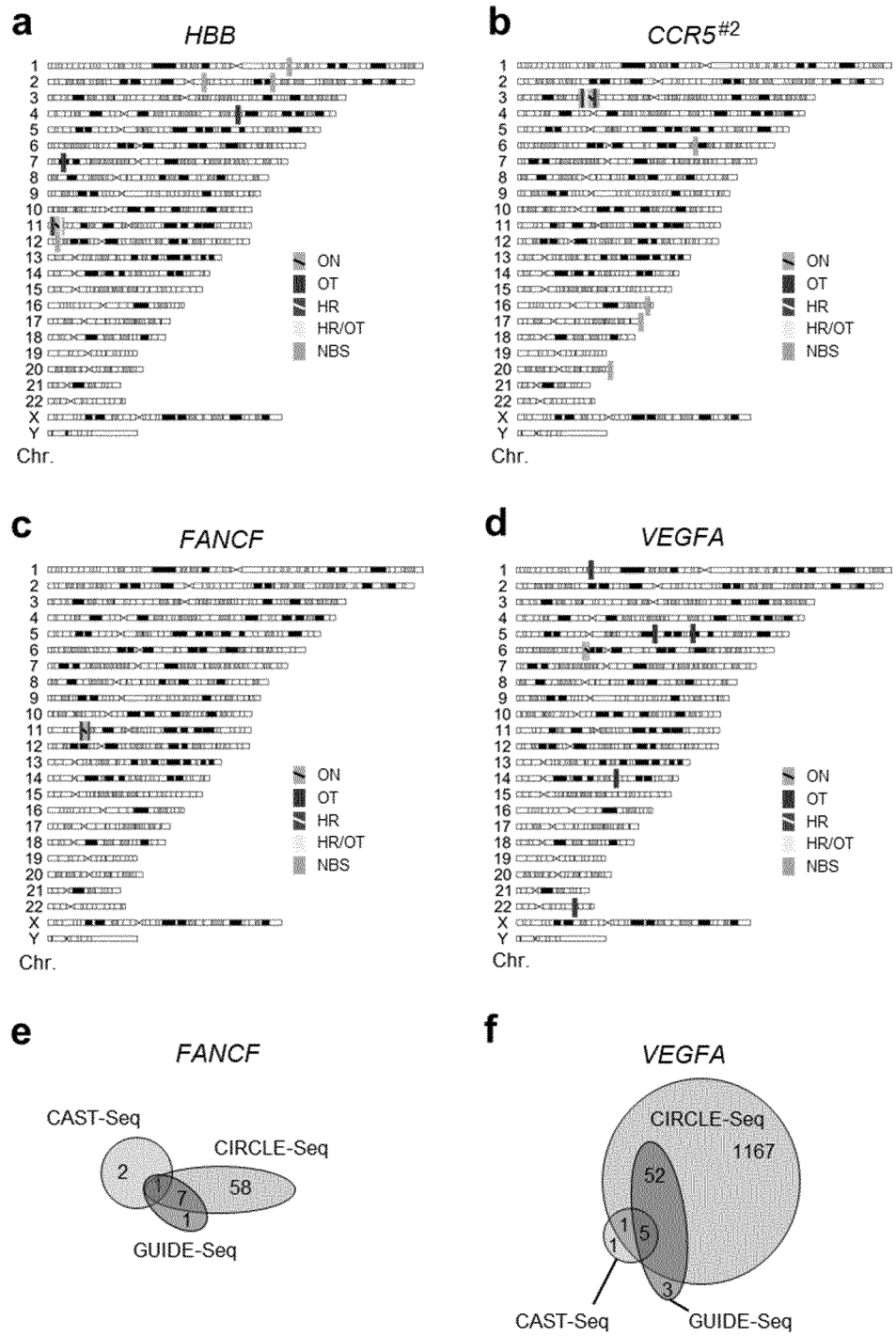

FIG. 9. CAST-Seq analysis of CRISPR-Cas9 or TALEN targeted genomic sites with more restrictive bioinformatics algorithm.

(a-d) Mapping of chromosomal aberrations. Chromosome ideograms reporting the CAST-Seq analysis of an HBB targeting TALEN pair (a) as well as CRISPR-Cas9 targeting CCR5[#2] (b), FANCF (c) and VEGFA (d). All relevant chromosomal aberration sites identified by CAST-Seq are highlighted. (e-f) Comparison with GUIDE-Seq and CIRCLE-Seq. Data obtained from CAST-Seq analysis of FANCF (e) and VEGFA (f) targeting CRISPR-Cas9 nucleases were compared with published GUIDE-Seq (PMC4320685) and CIRCLE-Seq (PMC5924695) data and visualized in Venn diagrams.

Figure 10:
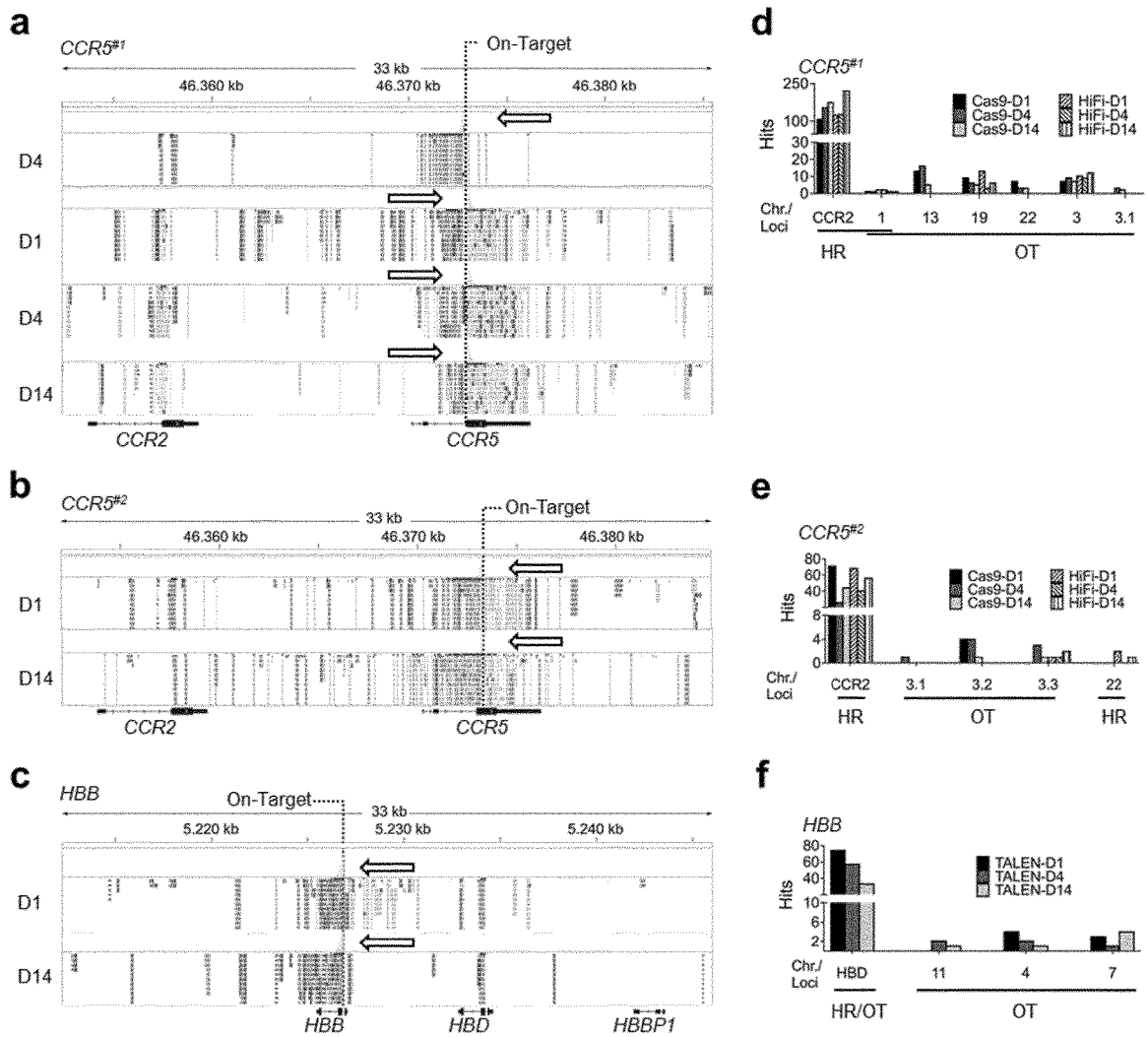

FIG. 10. Dynamics of chromosomal abberations.

(a-c) Qualitative visualization. Integrative Genomics Viewer (IGV) plots show target region, CCR5[#1] (a), CCR5[#2] (b) and HBB (c), within a window of 33 kb. Only top rows are shown. White arrows indicate bait orientation and dotted vertical lines the on-target site. Harvesting time in days post-electroporation (D1, D4, D14) is indicated on the left. (d-f) Quantitative analysis. Plots show number of clustered CAST-Seq reads (hits) for D1 to D14 samples of CRISPR-Cas targeting CCR5[#1] (d) and CCR5[#2] (e) or TALEN targeting HBB (f). Cluster category (HR and/or OT) is indicated.

Figure 11:
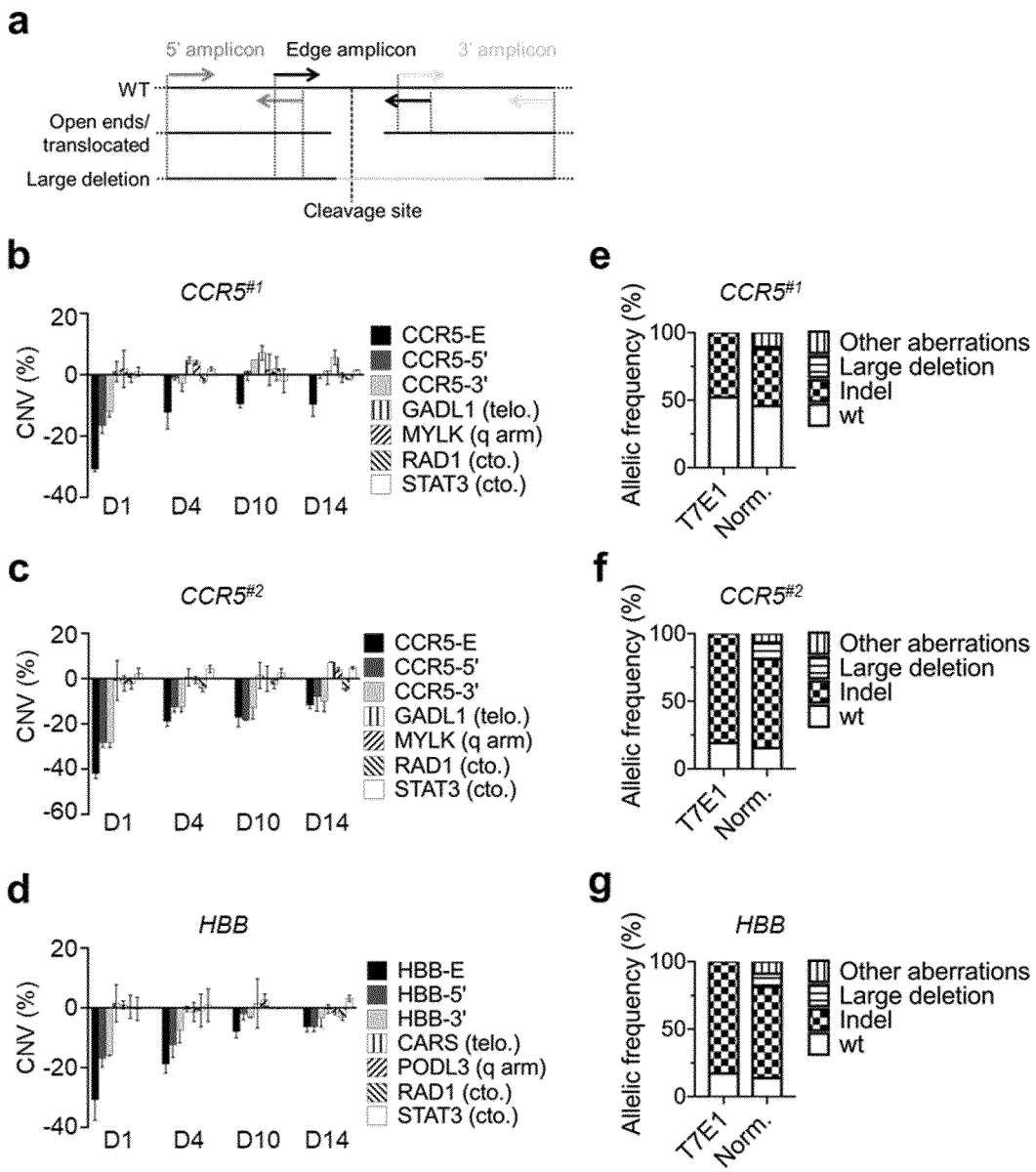

FIG. 11. DNA repair kinetics and quantification of chromosomal aberrations.

(a) ddPCR strategy. The 'edge amplicon' (~200 bp) encompass the cleavage site and is flanked by 5' or 3' amplicons to either site of the target site. Translocation are expected to reduce the amount of edge amplicon products, while large deletions will also reduce the quantity of the flanking amplicons. Amplicons positioned at the telomeric side (telo.) and the opposite chromosome arm (q arm) relative to the target site, as well as two control amplicons (cto.) on other chromosome, were used to establish the relative change of amplifiable on-target copies. (b-d) Variation of target site copy numbers. Plots show relative copy number variation (CNV) of amplifiable target sites in CD34+ cells edited with CRISPR-Cas targeting CCR5[#1] (b) or CCR5[#2] (c), or with a TALEN targeting HBB (d), at different time points (day 1 to day 14) after transfection. (e-g) Data summary. ddPCR results were used to normalize (Norm.) the indel frequencies determined by T7E1 assay for D4 time points. 'Large deletion' denotes the relative decrease of the average number of flanking amplicons while 'other aberrations' is specified as the relative difference between the number of edge amplicons and the average number of flanking amplicons.

TABLES

Table 1. ON-Target Sequences

Listed are the designer nuclease target sites in CCR5, VEGFA and FANCF.

Table 2. Primer and Linker Design

Listed are the deoxyoligonucleotides used to perform CAST-Seq to assess chromosomal aberrations in cells edited with CRISPR-Cas9 nucleases targeted to CCR5, VEGFA and FANCF. The sequences exemplified in Table 2 may serve as an example how the appropriate primers can be designed also for other on-target sites.

Table 3. Effect of Decoy Primers

To assess the impact of the decoy primers on the signal-to-noise ratio of CAST-Seq, side-by-side analyses were performed in the presence or absence of decoy primers. Data is based on all reads in clusters identified by CAST-Seq performed on genomic DNA isolated from CD34+ hematopoietic stem and progenitor cells that were edited with CRISPR-Cas9 nucleases either targeting the VEGFA locus or the FANCF locus.

Table 4: CAST-Seq Analysis for CCR5 Targeting CRISPR-Cas9 Nuclease

Listed are all sites identified by CAST-Seq (complete analysis, i.e. forward and reverse) in CD34+ hematopoietic stem and progenitor cells edited with a CRISPR-Cas9 nuclease targeting the CCR5 locus (target site: 5'-GT-GAGTAGAGCGGAGGCAGGAGG (SEQ ID NO:1, PAM underlined). The table reports the chromosomal location of the chromosomal aberration, the number of de-duplicated reads (hits), the number of reads, and the assigned category of the translocation event.

Table 5. Sensitivity of CAST-Seq

Droplet digital PCR (ddPCR) was used to quantify the number of large deletion events occurring between the CCR5 and the CCR2 loci in untreated cells and in hematopoietic stem cells edited with CRISPR-Cas9 nucleases targeting the CCR5 locus. 500 ng of genomic DNA contains about 152.000 haploid genomes.

Table 6: CAST-Seq Analysis for VEGFA Targeting CRISPR-Cas9 Nuclease

Listed are all relevant sites identified by CAST-Seq (exemplarily shown for forward analysis) in CD34+ hematopoietic stem and progenitor cells edited with a CRISPR-Cas9 nuclease targeting the VEGFA locus (target site: 5'-GGT-GAGTGAGTGTGTGCGTGTGG (SEQ ID NO:3), PAM underlined). The table reports the chromosomal location of the chromosomal aberration, the number of de-duplicated reads (hits), the number of reads, and the assigned category of the translocation event.

Table 7: CAST-Seq Analysis for FANCF Targeting CRISPR-Cas9 Nuclease

Listed are all relevant sites identified by CAST-Seq (exemplarily shown for forward analysis) in CD34+ hematopoietic stem and progenitor cells nucleofected with a CRISPR-Cas9 nuclease targeting the FANCF locus (target site: 5'-GGAATCCCTTCTGCAGCACCTGG (SEQ ID NO:4), PAM underlined). The table reports the chromosomal location of the chromosomal aberration, the number of de-duplicated reads (hits), the number of reads, and the assigned category of the translocation event.

Table 8. Software Used for CAST-Seq

Listed is all software used for CAST-Seq. The indicated versions were available at the priority date under the addresses provided.

Table 9. R Packages Used for CAST-Seq

Listed is the R package used for CAST-Seq. The indicated versions were available at the priority date under the addresses provided.

Table 10. Scoring Matrix

Scoring matrix of nucleotide substitution used for the alignment of translocation sites against the target site sequence, including weights for mismatch and bulges (insertions/deletions).

IUPAC code is used. A, adenine; C, cytosine; G, guanine; T (or U), thymine (or uracil); R, A or G; Y, C or T; S, G or C; W, A or T; K, G or T; M, A or C; B, C or G or T; D, A or G or T; H, A or C or T; V, A or C or G; N, any base.

Table 11. Primer Design for HBB Target Site (Targeted by TALEN)

The target sequence is shown as well as the relevant sequences required for amplification.

Table 12. Primer Design for CCR5 Target Site 2

The relevant target sequence and the sequences of the primers are shown.

Table 13. Primer Design for ddPCR

For several target sites the sequences of forward and reverse primers are provided.

DETAILED DESCRIPTION OF THE PREFERRED EMBODIMENTS

The present invention provides a novel method that is used to characterize the genomic modifications caused by the use of designer endonucleases in any eukaryotic cell type, including but not limited to human cells, non-human primate cells, mammalian cell types, vertebrate cell types, yeast, plant cells.

CAST-Seq can characterize chromosomal aberration caused by both off-target activity and on-target activity of designer nucleases. As such, it also provides a new diagnostic method to classify rare acentric/dicentric translocations derived from the fusion of two sister chromosomes at on-target sites, or large chromosomal deletions originating from the on-target cleavage site. Importantly, CAST-Seq can also detect designer nuclease induced chromosomal aberrations that initiate at common breaking sites (CBS) or naturally occurring breaking sites (NBS) in the genome.

In the context of clinical genome editing applications in humans, CAST-Seq can be effectively implemented during the preclinical phase to characterize the specificity of any endonuclease (e.g. but not limited to designer nucleases of the types CRISPR-Cas, TALEN, ZFN, MegaTAL) in order to choose e.g. an endonuclease that combines high activity with high specificity. In this context, CAST-Seq can also be used to characterize the impact of modifications introduced into a programmable endonuclease, such as modifications that affect affinity, specificity and/or stability of the endonuclease.

Moreover, because of the high sensitivity minimal amounts of genomic DNA are sufficient to perform a complete analysis. Hence, CAST-Seq can also be employed to characterize a manufactured gene editing product before its application to the patient as part of a quality control analysis.

CAST-Seq can also be employed in the patient follow up phase. E.g. CAST-Seq can be used to assess the genomic integrity of various peripheral blood cell types after transplantation of gene edited hematopoietic stem cells.

Moreover, since CAST-Seq is a semi-quantitative method, alteration in the frequencies of specific modifications can be followed overtime, e.g. to evaluate clonal expansion of certain modifications in early precancerous cells. Once enough data are available, this will also allow CAST-Seq to be used to predict the outcome and/or risk of genotoxic mutations on the development of cancer.

Applications of CAST-Seq include but are not limited to disorders for which ex vivo genome editing is applied, such as defects of the immune system, hemophilia, hemoglobinopathies, metabolic disorders, infectious diseases, and improvements to T cell based immuno-therapies to fight cancer.

CAST-Seq can also be implemented to assess the outcome of gene editing performed in vivo, i.e. by directly applying the genome editing tools to the patient through e.g. viral delivery or delivery by nanoparticles or any other means. In such a context, a small biopsy taken from the target organ (e.g. the liver) will be sufficient to assess the impact of designer nuclease induced genetic or chromosomal modifications. This approach can be applied not only to the target organ but could also be employed to assess the impact on gene editing approaches in off-target organs. Also, longitudinal studies can be employed to follow the fate of gene edited cells.

The method of the present invention may preferably be used in disorders for which in vivo genome editing is applied, such as hemophilia, metabolic disorders, genetic eye disorders, hereditary hearing disorders, inherited muscle disorders, neuromuscular diseases, and disorders affecting the central nervous system.

The present invention provides a novel diagnostic tool for the study of the cancer genome. Given a particular mutation or stimuli, CAST-Seq can map the common breaking site (CBS) and portray the mutation signature of a given cancerogenic model. By using CAST-Seq in such an approach, it will be possible to define new standard approaches to predict and diagnose cancer outcomes.

The method of the present invention relates to the detection of undesired modifications in a nucleic acid, preferably a genomic acid, which is caused by the activity of a designer nuclease.

Such modifications occur preferably at the so called "off-target sites" but can also occur at the so called "on-target site". In order to detect such undesired modifications, the method according to the present invention performs a nucleic acid amplification step which is preferably a PCR (polymerase chain reaction). Other suitable methods for amplifying nucleic acids like isothermal amplification methods ligase chain reactions, loop-mediated isothermal amplification, multiple displacement amplification or nucleic acid sequence based amplification (NASBA) can also be used.

In the first step, a library is prepared from eukaryotic cells that were exposed to a designer nuclease under conditions which allow the designer nuclease to introduce at least one DNA double strand break (step a). Suitable so-called designer nucleases are preferably CRISPR-Cas nucleases; TALEN; ZFN; MegaTAL, to name only a few.

The nucleic acid of the library is then converted into "random fragments" (step b). In a preferred embodiment, the fragments obtained have a length of about 350 base pairs. This means that the majority of the fragments ranges from about 200 to about 500 base pairs, whereby the median size of fragments is around 350 base pairs. The fragmentation can be obtained by physical measures like applying sheer forces or sonication or alternatively the fragmentation can also be obtained by digestion with suitable enzymes cutting the double-stranded nucleic acid at random sites. This step does not involve the action of defined restriction enzymes or of transposons.

In order to have uniform ends on each fragment, a repair is performed in order to obtain ends that are preferably modified to have a protruding A at the 3' end (step c). Those "random fragments" having a protruding A are then coupled with a suitable linker which has also a protruding 3' T which is complementary to the A of the repaired fragments. This improves the rate of ligation of the linker to the repaired ends of the "random fragments".

In a preferred embodiment, the linker comprises also a sequence which is complementary to the forward primer or the backward primer respectively. This construction allows an easy amplification of the fragment having the linker.

Then, a first nucleic acid amplification reaction is performed with a suitable "on-target primer" and a suitable "linker primer" which are complementary either to a sequence in close proximity to the on-target sequence or to a binding position which is preferably introduced by the linker. In a preferred embodiment, the binding sites of the on-target primers are located in a distance of at least 25 nucleotides, preferably of at least 35 nucleotides and more, preferably of at least 50 nucleotides upstream of the on-target site. Decoy primers enhance the sensitivity and the specificity of the method according to the invention.

In addition to the forward and backward primer, at least one, preferably at least two decoy primers are added. The purpose of the decoy primers is to suppress or to at least substantially reduce the amplification of such fragments which only contain on-target sequences on a "random fragment" i.e. that do not contain a chromosomal aberration event. When the amplification of fragments containing the on-target is reduced, there is a higher chance to identify off-target sites because the number of such off-target site containing fragments is increased compared with the fragments containing only on-target sequences. An "on-target primer" is a primer which binds specifically to the on-target site. It has a high identity and a sufficient length in order to provide high specificity in binding.

In a preferred embodiment of the present invention, there are used at least two different decoy primers, whereby both decoy primers are complementary to sequences in close vicinity downstream of the on-target site. Depending on the specific sequences surrounding the desired on-target site, the sequences to which the decoy primer are complementary should be selected. In a preferred embodiment, the binding sites of the decoy primers do not overlap. In a preferred embodiment, one primer is complementary to the top strand of the DNA sequence while the other primer is complementary to the bottom strand of the DNA sequence. Preferably, the sequences are located in a distance of at least 10 nucleotides, preferably of at least 15 nucleotides and more, preferably of at least 30 nucleotides downstream of the on-target site. The optimal conditions of the location of the sequences suitable for binding to the decoy primers have to be evaluated for each on-target site. The effect obtainable by using the decoy primers is that the occurrence of amplified sequences containing the on-target site are reduced and that thereby the probability of detecting off-target sites is substantially increased. Since the sequences upstream and downstream of the on-target site are known, a suitable sequence for the decoy primer can be easily selected. Preferably, the decoy primers are not blocked at either end in order to allow the polymerase to extend the decoy primers.

The sequences obtained by the method according to the present invention are then subjected to high-throughput sequencing and the information of the obtained sequences is analyzed with the bioinformatic measures which are well known to the persons skilled in the art.

While methods to detect off-target activity or nuclease-induced chromosomal aberrations have been previously described, the method according to the present invention, short as CAST-Seq, is a fundamental new tool for clinical risk assessment in therapeutic genome editing by inclusion of some critical novel features.

The advantages obtainable by the method of the present invention are in particular:
(i) highly sensitive and highly specific,
(ii) quantitative,
(iii) able to detect previously undescribed types of chromosomal aberrations, and
(iv) can be performed directly in the clinically relevant cell type.

The advantageous properties are disclosed in the examples described herein:
(i) Higher Sensitivity and Specificity The present data indicate that CAST-Seq is able to detect 10 translocation events (=1 hit) in 150,000 haploid genomes (500 ng of genomic input DNA), corresponding to a lower limit of detection (LLoD) of about 0.007%. This high sensitivity, including a higher specificity, could be reached by the use of DECOY primer, which are described for the first time in the present approach.
(ii) Quantitative Chromosomal breaking points in combination with the adapter ligation site, create unique molecular identifiers, which allows the determination of a number of individual translocations, to cluster them into events that are prompted by a particular trigger, and to quantify the frequencies of very rare events based on the known amount of input genomes. The linear correlation between the numbers of CAST-Seq hits and the actual number of chromosomal rearrangements, as determined by quantitative ddPCR, confirms the quantitative nature of the method and its high sensitivity.
(iii) Previously not Described Chromosomal Aberrations CAST-Seq identified for the first time chromosomal rearrangements not related to off-target activity of a designer nuclease. In particular, it was found that nuclease induced DNA double strand breaks are just one of the factors that drives translocations. CAST-Seq demonstrates for the first time that regions that share substantial homology to the on-target gene, even if they do not contain an off-target site, are likely subject to chromosomal rearrangements.
(iv) Performed in Clinically Relevant Cell Type Unlike HTGTS/UDiTaS, it has been demonstrated that CAST-Seq can be performed on genomic DNA harvested from gene-edited hematopoietic stem cells, i.e. a clinically relevant cell type.

The method according to the present invention is further illustrated and described in the figures, tables and experiments. The person skilled in the art is well aware that the disclosed results represent preferred embodiment, whereby single features of the experiments or figures can easily be combined with other features disclosed in other experiments herein. It is usually not necessary that all features of one example can only be used together.

In another embodiment the present invention relates also to kits for performing a method of the present invention. Such kit comprises the necessary components required for performing the specific method described herein. In particular the kit contains the primers, the specific linkers and the decoy primers and the enzymes required for performing the reaction. All components described in the methods disclosed herein can be contained alone or together in such kit.

The results of the experiments using the method of the present invention shown in the Figures and Tables can be interpreted as follows:

The identification of rare designer nuclease induced mutagenic events, such as off-target mutagenesis, translocations, large deletions or large inversions, by high-throughput sequencing poses various challenges. In order to be cost-effective, the method should be based on minimal sequencing requirements without compromising on sensitivity. In order to be of clinical relevance, the method should be applicable to patient-derived cells rather than be performed in a surrogate cell line with a different genetic and epigenetic background. Furthermore, the test should be able to run on minimal input of genomic DNA, so it can be performed on precious cell material derived from the patient. Finally, technical and analysis biases, such as PCR amplification biases and flaws in the bioinformatics pipeline, must be kept to a minimum to avoid false positive or false negative results.

CAST-Seq was developed to meet these requirements and to identify rare chromosomal aberration events with unprecedented sensitivity. To this end, CAST-Seq employs a 3-step PCR strategy that includes the use of nested as well as decoy primers, respectively. A schematic overview of CAST-Seq is shown in FIG. 1. After the isolation of genomic DNA from cells exposed to designer nucleases, the genomic DNA is fragmented using focused ultrasonication or enzymatic digestion to produce fragments with an average size of 350 bp. After end repair and ligation of linkers to either end, a $1^{st}$ PCR step is performed that includes a target site specific primer (ON-target primer, Table 2), a primer binding to the linker (linker primer, Table 2), and one or two decoy primers (Table 2). Decoy primers are designed to bind in close proximity to the target site but on the opposite site with respect to the ON-target primer. They are added to the reaction to prevent the generation of full-length amplification products from templates derived from non-translocation events (FIG. 1a right hand side, FIG. 3). The decoy primers cannot bind to templates derived from translocation (or other chromosomal aberration) events (FIG. 1a left hand side) and therefore do not prevent their amplification. For the $2^{nd}$ PCR step two nested primers (ON-target nested primer and linker nested primer, Table 2) that contain adapters for the $3^{rd}$ PCR are used. Decoy primer derived products (FIG. 1a right hand side) will not be amplified in this step. Finally, the $3^{rd}$ PCR is used to add the Illumina adapters and barcodes for NGS.

The bioinformatics pipeline to identify and annotate chromosomal aberration events is schematically shown in FIG. 1b and described in detail in Example 2. CAST-Seq was designed not only to detect translocation events but also other chromosomal aberrations, including large deletions and sequence inversions, in a semi-quantitative way. Events annotated to a specific chromosomal region are likely to derive from a single mode of action, either directly or indirectly related to designer nuclease ON-target or OFF-target activity. Such events are defined as clusters if at least 2 de-duplicated reads within a distance of 2,500 bp occurred. In order to calculate the likelihood of a read to fall into one cluster by chance, rather than by a certain mode of action, the analyzed CAST-Seq sample was compared to an in silico created random read library that contains the same number of reads (FIG. 2). The distribution of the distance of consecutive reads is exemplarily shown for a CAST-Seq analysis performed on hematopoietic stem cells edited with CCR5 targeting CRISPR-Cas9 nucleases in comparison to an untreated sample and the random control library (FIG. 2a). In this example, the 2,500-bp threshold line describes an area of <5% in the random library, meaning that the likelihood of a read to fall into one cluster by chance is smaller than 5%.

When assessing CAST-Seq results, we realized that not all identified chromosomal aberration events could be directly linked to designer nuclease OFF-target activity. A DNA repair pathway active in most cells is homology-directed repair. Homology-directed repair is based on homologous recombination (HR) between homologous DNA regions to repair the damaged site. Often, the sister chromatid is used in this process for perfect repair but other homologous sequences can be recruited as well. Hence, an ON-target cleavage event can trigger inter-chromosomal or intra-chromosomal (including large deletions and sequence inversions) translocation with homologous regions in the genome. Finally, a designer nuclease induced DNA double strand break at the ON-target site can also trigger recombination with naturally occurring DNA breaks in the genome. Based on whether an OFF-target site could be identified and on the extent of homologous sequences found at the translocation site, the identified events were classified as OFF-target (OT), homology-mediated recombination (HR), or common breaking site (CBS)-mediated translocation. The underlying bioinformatics is described in Example 3. In brief, the designer nuclease target sequence is aligned to the CAST-Seq cluster regions and the best alignment score is selected. An in silico random library is cross-examined the same way in order to test whether the alignment score passes the 5% threshold (FIG. 2b). All clusters passing this threshold were classified as designer nuclease OT-triggered translocation. For all clusters not meeting this requirement, a 5 kb window surrounding the translocation event was interrogated for sequences homologous to the target site and compared to the random library to define the common length threshold. A translocation event was categorized as HR if the length of the flanking regions was higher than the 5% longest substrings in the random sequences (FIG. 2c). All other clusters were labeled as CBS-triggered translocation.

The CAST-Seq decoy strategy was designed to reduce background reads derived from non-modified target sites and it can be easily implemented for every chosen target site. Its efficiency was exemplarily shown for the CCR5 target site (FIG. 3a). Two decoy primers in forward (F) and reverse (R) orientation were used. If decoy primers were modified by 3'-phosphorylation to block 3'-extension, they were able to reduce but not completely block the formation of the full-length amplicons of 412 bp (FIG. 3b). When unmodified decoy primers were added to the reaction, however, the generation of the full-length amplicon was effectively prevented (FIG. 3c). Instead, two products with expected sizes of 264 bp and 140 bp were generated. Finally, even the presence of a single decoy primer was sufficient to effectively abolish the generation of full-length amplicons (FIG. 3d), demonstrating the efficacy of the decoy strategy. To estimate the overall effectiveness of this strategy, side-by-side CAST-Seq analyses were performed for CRISPR-Cas nucleases targeting either VEGFA or FANCF in the presence or absence of decoy primers. When considering all translocated sequences with the exception of reads derived from the ON-target cluster, about a 5-fold increase in the signal-to-noise ratio was observed (Table 3).

To illustrate the potential of this new method, CAST-Seq was performed on genomic DNA isolated from hematopoietic stem cells that were edited with CCR5 targeting CRISPR-Cas9 (Table 4, FIG. 4). All identified translocation events, stratified in OT, HR and CBS, are shown in a chromosome plot (FIG. 4a). Of note, the majority of OT sites contain more than 5 mismatches in combination with bulges (FIG. 4b).

A closer look at the top-30 aligned clusters enabled further analysis, such as the locations of mismatches and bulges as well as the characterization of the PAM identified in OFF-target sites (FIG. 5a). Of note, while all OFF-target site PAMs had a G in position 3, two OT sites did not contain a purine (R: A or G) in position 2. Furthermore, 2 out of 30 sites tolerated a −1 bulge in position 1. As reported earlier, the tolerance to accept mismatches and bulges is more pronounced in the PAM-distal region of the targeted site. A logo analysis (FIG. 5b) shows the consensus sequence of the OFF-target sites, confirming less promiscuity in the PAM-proximal region. This observation was further corroborated by a quantitative analysis performed on target site subgroups (FIG. 5c). Hence, CAST-Seq mediated target sequence alignment replicates the previously reported findings that the most conserved regions in CRISPR-Cas9 target sites are the nucleotides in the PAM and in the PAM-proximal region. On the other hand, CAST-Seq identified new features regarding tolerance to mismatches and bulges in the PAM sequence.

As mentioned above, chromosomal aberrations can also be triggered by designer nuclease ON-target activity. The CCR2 locus is located adjacent to the CCR5 target locus and shares high sequence homology to CCR5. A closer inspection of this region revealed an extensive number of chromosomal aberrations surrounding the CCR5 ON-target cleavage site (FIG. 6a). Of note is a hotspot in the CCR2 gene that was annotated by CAST-Seq as a large deletion induced by HR (FIG. 6b). Genotyping by T7E1 assay confirmed that this site was not cleaved by CRISPR-Cas9, confirming that ON-target activity can trigger chromosomal aberrations by enhancing recombination between homologous sequences.

Since CAST-Seq has a forced sequencing orientation, it is possible to define the orientation of translocation events. CAST-Seq hence allowed us to identify additional chromosomal aberrations triggered by ON-target activity, such as inter-chromosomal translocations that led to the formation of acentric and dicentric chromosomes (FIG. 6c). In summary, CAST-Seq can identify various chromosomal aberrations, including events that were not described previously by other methods.

This comprises chromosomal aberrations triggered by ON-target activity, such as reciprocal translocations to homologous chromosomes leading to the formation of acentric/dicentric chromosomes, large insertion/deletions and inversions.

To evaluate the sensitivity of CAST-Seq, we assessed the rare recombination events between CCR5 and CCR2 on genomic DNA edited by CCR5 targeting CRISPR-Cas9 nucleases or in the untreated control. Using 500 ng of genomic DNA, the recombination event was detected in both samples with 60 or 63,011 reads, respectively (Table 5). In order to determine the copy number of fused CCR2-CCR5 loci in those samples, a quantification with droplet digital PCR (ddPCR) was performed by placing one primer on CCR5 and the other one on CCR2. The assay returned 9.8 copies in the untreated sample and 1,280 copies in the CRISPR-Cas9 edited sample. This means that CAST-Seq was able to detect 9.8 chromosomal aberration events in approximately 152,000 haploid genomes, corresponding to a sensitivity of ~0.006%. Since the sensitivity of CAST-Seq is directly proportionated to the number of analyzed cells, even higher sensitivities (i.e. <1:10,000) may be achievable by increasing the number of cells used to isolate the genomic DNA and, in consequence, be able to process more genomic DNA by CAST-Seq.

To verify that CAST-Seq can be applied to other target loci, hematopoietic stem cells were also edited with CRISPR-Cas9 nucleases targeting the VEGFA and FANCF loci. The results of these experiments are shown in Table 6 and Table 7, respectively.

Example 1: CAST-Seq Library Preparation

Genomic DNA from untreated and genome edited hematopoietic cells is extracted with QIAmp DNA Blood Mini Kit (Qiagen) and subsequently fragmented by sonication (Covaris) or by an enzymatic reaction (NEBNext® Ultra™ II FS DNA Library Prep Kit, NEB) in order to obtain DNA fragments with an average size of about 350 bp (see FIG. 1a). The fragmented genomic DNA is subsequently end repaired and A-tailed (NEBNext® Ultra II End Repair/dA-Tailing Module kit, NEB). Linker DNA, generated by annealing of two asymmetric deoxyoligonucleotides bearing either a 3'-T overhang on the plus strand or a 5'-phospho group in combination with a 3'-C7-amino group on the minus strand, is then ligated to the sheared DNA and subsequently purified with QIAquick PCR Purification Kit (Qiagen). In the first PCR round, 500 ng of DNA are mixed with decoy oligos as well as a linker-specific and a target site-specific primer. PCR is performed using the following conditions: 20 cycles of 95° C. for 15 sec, 63° C. for 20 sec, 72° C. for 20 sec. In the second PCR round, a nested PCR is performed with a linker-specific and a target site-specific primer harboring Illumina adapter sequences at their 5'-ends using the following conditions: 20 cycles of 95° C. for 15 sec, 68° C. for 20 sec, 72° C. for 20 sec. After amplification, the PCR reaction is purified with QIAquick PCR Purification Kit (Qiagen) and quantified with NanoDrop (ThermoFisher). For both rounds, Hot-start Q5 polymerase (Q5® High-Fidelity DNA Polymerase, NEB) was utilized in 50 μl reactions. Illumina barcoded adapters are added by a 7 cycle PCR reaction using NEBNext® Multiplex Oligos for Illumina (NEB) according to the standard protocol. The amplicons (~0.1-1 μg) are then purified with AMPure XP magnetic beads (Beckman Coulter) diluted to 4 nM and quantified by ddPCR using 'ddPCR Library Quantification Kit for Illumina TruSeq' (BIORAD) according to the manufacturer instruction. A final concentration of 8-10 pM of denatured DNA in 600 μl is finally loaded in a MiSeq Reagent Kit v2 cartridge (Illumina) and sequenced.

Example 2: Bioinformatic Analysis

Paired-end reads from Illumina high-throughput sequencing were merged using FLASh (v1.2.11) (https://ccb.jhu.edu/software/FLASH/) with 10 and 250 as minimum and maximum overlap, respectively. BBmap (version 38.22) (https://sourceforge.net/projects/bbmap/) was used next to first apply a positive selection of reads that contain the designer nuclease target site in order to eliminate PCR mispriming products. Afterwards, the reads were trimmed in order to eliminate the linker sequences, the Illumina adapter sequences, and the targeted elongation sequence (FIG. 1b). A check for short targeted sequence inversion was performed at the end of the filtering procedure using BBmap. Parameters were settled as follow: kmer length for finding contaminants was defined according to the nuclease target site, linker or primer length. Up to 2 mismatches and/or bulges were allowed in the reference kmers. Parameters not mentioned here are set to default. The selected reads were then aligned to the human reference genome (GRCh38/hg38) with Bowtie2 (version 2.3.4.2) (http://bowtie-bio.sourceforge.net/bowtie2/index.shtml) using the -very-sensitive preset of parameters to ensure the most reliable alignment. Low quality alignments were removed to reduce the possibilities of identifying false positive translocation sites (MAPQ<15). Software used for FASTQ processing is detailed in Table 8. Downstream analyses were performed with in-house R scripts. The list of R packages dedicated to genome annotation can be found in Table 9. The aligned reads were then deduplicated according to chromosome number, start, end and strand values. Reads that fall within 2 bp for start and end, respectively, were considered as "duplicated" reads and therefore deduplicated. Subsequently, the translocation point was determined and used for cluster analysis by comparing the distance distribution of consecutive reads with an in silico generated library that contains an equivalent number of random sites. The cluster error rates were quantified with the distance distribution curve of a randomized library (FIG. 2). A threshold distance of 2,500 bp was applied to achieve a significant p-value ($p<0.05$) in all our tested samples. Relevant clusters derived from the treated sample were then compared to the ones in the untreated sample to subtract the background. A hypergeometric test was performed to assess the significance of the difference between gene-edited and non-treated control samples by comparing the number of reads to the population size (i.e. total number of reads in the raw FASTQ files). Significant clusters were selected according to the adjusted p-value ($p<0.05$). Finally, each cluster containing only 1 deduplicated read is rejected.

Example 3: Classifying Translocation Events

The translocation sites were divided into three categories: OFF-target (OT) activity derived translocations, homologous recombination (HR)-mediated translocations, and common breaking site (CBS)-derived translocations (FIG. 2). To allocate each site to one of these categories, we compared a 500-bp genomic region surrounding the translocation sites against 10,000 random sequences of 500-bp. Next, every single site derived from real or random sequences was aligned to the designer nuclease target sequence, with a score between 1 for match and -1 for mismatch, gap opening and gap extension (Table 10), and the best match from forward and reverse complement sequences was selected. Next, the longest common substring between each sequence, including left and right flanking regions, was searched in forward and reverse complement sequences within a 5 kb window. Each event was finally categorized as follows: OT, if the target sequence alignment score of the sequence was higher than the 5% best score in the random sequences. HR, if the event was not OT but if the length of the flanking regions was higher than the 5% longest substring in the random sequences. All other events that did not fulfil these criteria were classified as CBS.

Example 4: More Restrictive Bioinformatic Analysis (FIG. 7)

Alignment: Mate paired reads from Illumina miSeq sequencing were merged using FLASH software (Bioinformatics 27 (2011) 2957-2963). BBmap (https://sourceforge.net/projects/bbmap/) was used for filtering and trimming as follow: merged reads containing the designer nuclease target site were filtered-in, whereas PCR mispriming products reads were filtered-out. Linker sequences, Illumina adapter sequences, targeted elongation sequence and bad quality reads were trimmed. Selected reads were aligned to the human genome GRCh38 (hg38) using Bowtie2 (Nat. Methods 9 (2012) 357-359) and the very-sensitive preset parameters to maximize the alignment accuracy. To reduce the probability of finding false positives, aligned reads with good mapping quality (MAPQ>15) were selected.

The aligned BAM file was converted into bed file using BEDTools (Bioinformatics 26 (2010), 841-842).

Deduplication/cluster definition: Reads located on the same coordinates were considered as PCR-derived duplicates and therefore deduplicated. To cope with translocation point or linker ligation sequencing/alignment biases, a tolerance of +/−3 bp was added. Hence, all reads within this +/−3 bp window were deduplicated and the total amount of reads was stored to quantify the translocation event. High reads density regions were determined using a random set of regions of the human genome to estimate distance distribution between two consecutive reads. A threshold distance of 2,500 bp achieved a significant p-value (p<0.05) in all tested samples. Subsequently, consecutive reads separated by less than 2,500 bp were merged into clusters, representing all putative translocation sites. When comparing more than one replicate for a sample, two proximal clusters were merged during the bioinformatic process (CCR5/CCR2 and HBB/HBD), and the individual clusters were manually recovered by re-setting the borders. Finally, the significance of the identified clusters was evaluated compared to a non-treated control sample using a Fisher's exact test. Significance threshold was set for adjusted p-value (Benjamini-Hochberg) below 0.05.

Translocation event classification: Translocation sites were classified into three groups: off-target (OT) and homologous recombination (HR)-mediated translocations, and naturally occurring breaksite (NBS)-derived translocations. To assess statistical significance of the groups, a set of 10,000 randomly chosen human genome sequences of 500 bp length was chosen. For OT, translocation sites were aligned to the on-target sequence. A nucleotide substitution matrix using +1 and −1 as weights for match and mismatch, respectively, was built. Gaps were allowed with the same penalty weight as mismatch. A pairwise alignment from Biostrings R Package (https://rdrr.io/bioc/Biostrings/) with "local-global" type of alignment was used. OT alignment scores were calculated for identified translocation sites and random sequences. For HR, the longest common substring (LCS) between left and right flanking regions, defining a surrounding window of 5 kb around the translocation site, and the know 5 kb window around the expected on-target, was chosen. Random sequences were used to estimate the length of LCS between the on-target and random regions. Finally, every single translocation site was categorized as follow: OT if OT alignment score was higher than the top 5% scores on random sequences; HR if LCS longer than the top 5% LCS in random sequences; NBS otherwise.

Annotation. Selected translocation sites were annotated with the nearest gene or gene region (e.g. promoter, exon, intron, etc.), based on distance to transcriptional start site (TSS) reported in the Bioconductor Annotation Package TxDb.Hsapiens.UCSC.hg38.knownGene (http://bioconductor.org/packages/TxDb.Hsapiens.UCSC.hg38.knownGene/). The whole set of genes that is located within a window of 100 kb around the translocation site is reported, specifically highlighting cancer-related genes based on the OncoKB database (JCO Precis Oncol. 2017, 1-16).

Example 5: Molecular Analyses

For analysis by digital droplet PCR (ddPCR), 150-550 ng of genomic DNA were digested with 5 U of HindIII HF or AvrII (NEB) at 37° C. for 30 min to reduce sample viscosity. After digestion, either 100 ng (translocation) or 20 ng (large deletion) of digested genomic DNA were added to the ddPCR reaction mix containing QX200™ EvaGreen ddPCR Supermix™ (Bio-Rad, Cat. #1864034). Each reaction was complexed with 100 nM of primers and loaded into the QX200 Droplet Generator (Bio-Rad). The generated droplets were transferred to a 96-well PCR plate (Bio-Rad, Cat. #12001925) and the plate sealed with a PX1 PCR plate sealer (Bio-Rad). For all assays, endpoint PCR was performed as follows: lid preheat at 95° C. for 5 min, 50 cycles of 95° C. for 30 s, 62° C. for 60 s, 72° C. for 2 min, followed by 5 min at 4° C. and 5 min at 90° C. (ramping rate set to 2° C./s). After PCR, data was acquired in a QX200 Droplet Reader and results analyzed with QuantaSoft™ Analysis Pro (Bio-Rad). Results were considered significant if at least 10,000 droplets/20 µl reaction were generated. To calculate the frequencies of 'large deletions' and 'other aberrations' in edited samples, the average ddPCR value of a technical duplicate was first normalized to the untreated matched control sample to minimize assay-to-assay variation, and then normalized for the amount of genomic input DNA by dividing the number by the average of the two values obtained for the control genes (RAD1, STAT3). The average value from 5' and 3' assays was used to determine the fraction of large deletions. The fraction of translocations was calculated by subtracting the fraction of large deletions from the 'Edge' value. The indel percentage from T7E1 assay was recalculated based on the formula: (100−(large deletion× 100)−(translocation×100))×indel %.

TABLE 1

| ON-Target Sequences | | |
|---|---|---|
| Seq ID | Sequence (5'→3') | Remark |
| 1 | GTGAGTAGAGCGGAGG CAGG<u>AGG</u> | CCR5 target site (PAM underlined) |
| 2 | GTGAGTAGAGCGGAGG CAGG<u>NRG</u> | CCR5 target consensus site (PAM underlined) |
| 3 | GGTGAGTGAGTGTGTG CGTG<u>TGG</u> | VEGFA target site (PAM underlined) |
| 4 | GGAATCCCTTCTGCAG CACC<u>TGG</u> | FANCF target site (PAM underlined) |

TABLE 2

Primer and Linker Design

| Purpose/Target | function | | ID# | Sequence 5'→3' | SEQ ID NO. |
|---|---|---|---|---|---|
| Linkers | Linker ligation | positive strand | 4038 | GTAATACGACTATAGGGCTCCGCTTAAGGGACT | 5 |
| | | negative strand | 4039 | P-GTCCCTTAAGCGGAGC-NH3 | 6 |
| Linker primer | 1st PCR | linker | 4032 | GTAATACGACTCACTATAGGGC | 7 |
| | 2nd PCR | linker, nested | 4033 | ACACTCTACACTCTTTCCCTACACGACGCTCTTCCGATCTAGGGCTCCGCTTAAGGGAC | 8 |
| CCR5 reverse primer (centromeric side) | 1st PCR | On-target | 4034 | AGGTAGATGTCAGTCATGCT | 9 |
| | | decoy fwd | 4036 | ATCAATGTGAAGCAAATCGCA | 10 |
| | | decoy rev | 4037 | AGGGCTCCGATGTATAATAATTG | 11 |
| | 2nd PCR | ON-target, nested | 4035 | GACTGGAGTTCAGACGTGTGCTCTTCCGATCTGCTCTTCAGCCTTTTGCAGTTTATCAG | 12 |
| CCR5 forward primer tetomeric side | 1st PCR | ON-target | 4272 | GGATTATCAAGTGTCAAGTCC | 13 |
| | | decoy fwd | 3779 | CTGGTCATCCTCATCCTG | 14 |
| | | decoy rev | 4261 | AAAACCAAAGATGAACACCAGT | 15 |
| | 2nd PCR | ON-target, nested | 4262 | GACTGGAGTTCAGACGTGTGCTCTTCCGATCTATACATCGGAGCCCTGCCA | 16 |
| Vegfa primer | 1st pcr | ON-target | 4382 | GAGAGGGACACACAGATC | 17 |
| | | decoy fwd | 4380 | CGTCTTCGAGAGTGAGGAC | 18 |
| | | decoy rev | 4381 | CTGCTCGCTCCATTCAC | 19 |
| | 2nd PCR | ON-target, nested | 4383 | GACTGGAGTTCAGACGTGTGCTCTTCCGATCTACACAGATCTATTGGAATCCTGGAGTG | 20 |
| FANCF primer | 1st PCR | ON-target | 4362 | GTTCCAATCAGTACGCAG | 21 |
| | | decoy fwd | 4360 | CTTGAGACCGCCAGAAG | 22 |
| | | decoy rev | 4361 | CACTACCTACGTCAGCAC | 23 |
| | 2nd PCR | ON-target, nested | 4363 | GACTGGAGTTCAGACGTGTGCTCTTCGATCTGCCGTCTCCAAGGTGAAAGC | 24 |

TABLE 3

Effect of decoy primers.

| Target | OFF-TARGET READS (AVERAGE FOLD CHANGE) | STDEV |
|---|---|---|
| VEGFA | 5.1 | ±0.4 |
| FANCF | 5.0 | ±0.2 |

To assess the impact of the decoy primers on the signal-to-noise ratio, side-by-side CAST-Seq analyses were performed in the presence or absence of decoy primers. The fold change was calculated using the formula below:

$$\frac{\text{(total reads in clusters with decoy} - \text{reads in ON-target cluster with decoy)} / \text{total reads with decoy}}{\text{(total reads in clusters without decoy} - \text{reads in ON-target cluster without decoy)} / \text{total reads without decoy}}$$

TABLE 4

CAST-Seq analysis for CCR5 targeting CRISPR-Cas9 nuclease

| Chromosome | Start | End | Hits | Reads | Category |
|---|---|---|---|---|---|
| chr3 | 46367384 | 46381002 | 13684 | 2564351 | ON-TARGET |
| chr13 | 24886065 | 24888172 | 69 | 5930 | OFF-TARGET |
| chr19 | 35352634 | 35353338 | 17 | 7538 | OFF-TARGET |
| chr11 | 133747455 | 133747970 | 8 | 6045 | OFF-TARGET |
| chr10 | 11712420 | 11712929 | 8 | 518 | OFF-TARGET |
| chr3 | 33147914 | 33148416 | 7 | 211 | OFF-TARGET |
| chr22 | 29073798 | 29074309 | 7 | 208 | OFF-TARGET |
| chr2 | 27731141 | 27731654 | 6 | 2916 | OFF-TARGET |
| chr11 | 396300 | 396818 | 6 | 849 | OFF-TARGET |
| chr3 | 192973003 | 192973517 | 5 | 69 | OFF-TARGET |
| chr12 | 52697472 | 52697979 | 4 | 417 | OFF-TARGET |
| chr6 | 1490592 | 1491094 | 4 | 302 | OFF-TARGET |
| chr10 | 91608416 | 91608926 | 4 | 138 | OFF-TARGET |
| chr16 | 9384008 | 9384516 | 4 | 47 | OFF-TARGET |
| chr2 | 7907009 | 7907511 | 4 | 13 | OFF-TARGET |
| chr2 | 203870062 | 203870562 | 3 | 3621 | OFF-TARGET |
| chr16 | 3054688 | 3055207 | 3 | 66 | OFF-TARGET |
| chr3 | 46356995 | 46358671 | 694 | 63011 | HR |
| chr3 | 46360849 | 46364874 | 19 | 4431 | HR |

TABLE 4-continued

CAST-Seq analysis for CCR5 targeting CRISPR-Cas9 nuclease

| Chromosome | Start | End | Hits | Reads | Category |
|---|---|---|---|---|---|
| chr3 | 37046851 | 37047366 | 12 | 217 | HR |
| chr1 | 235196336 | 235196844 | 6 | 364 | HR |
| chr1 | 220970449 | 220970959 | 5 | 90 | HR |
| chr2 | 108473896 | 108474401 | 5 | 13 | HR |
| chr19 | 11128451 | 11128957 | 4 | 155 | HR |
| chr3 | 46351798 | 46352301 | 4 | 92 | HR |
| chr1 | 233407233 | 233407736 | 4 | 53 | HR |
| chr13 | 20707652 | 20708155 | 2 | 396 | HR |
| chr11 | 87001121 | 87001628 | 2 | 320 | HR |
| chr2 | 70200237 | 70200737 | 2 | 16 | HR |
| chr4 | 126697877 | 126698400 | 22 | 1344 | CBS |
| chr1 | 15404594 | 15405115 | 13 | 2861 | CBS |
| chr3 | 45888052 | 45888571 | 13 | 418 | CBS |
| chr7 | 148990482 | 148991011 | 13 | 168 | CBS |
| chr7 | 5397004 | 5397524 | 12 | 269 | CBS |
| chr8 | 105275605 | 105276115 | 11 | 890 | CBS |
| chr19 | 44844225 | 44844734 | 11 | 618 | CBS |
| chr7 | 36875934 | 36876451 | 11 | 193 | CBS |
| chr3 | 173891336 | 173891854 | 10 | 502 | CBS |
| chr4 | 56315538 | 56316061 | 10 | 79 | CBS |
| chr7 | 45528063 | 45528572 | 10 | 32 | CBS |
| chr18 | 31539684 | 31540191 | 9 | 3630 | CBS |
| chr2 | 47793539 | 47794039 | 9 | 3174 | CBS |
| chr1 | 1535558 | 1536071 | 9 | 1052 | CBS |
| chr13 | 58455707 | 58456225 | 9 | 461 | CBS |
| chr2 | 172156140 | 172156661 | 9 | 109 | CBS |
| chr2 | 12715962 | 12716463 | 8 | 1461 | CBS |
| chr10 | 132462758 | 132463271 | 8 | 927 | CBS |
| chr16 | 85033587 | 85034097 | 8 | 514 | CBS |
| chr11 | 55807139 | 55807651 | 8 | 468 | CBS |
| chr2 | 183611509 | 183612020 | 8 | 368 | CBS |
| chr18 | 50028215 | 50028720 | 8 | 339 | CBS |
| chrX | 96709289 | 96709797 | 8 | 286 | CBS |
| chr1 | 168791914 | 168792420 | 8 | 109 | CBS |
| chr3 | 64787649 | 64788160 | 8 | 48 | CBS |
| chr5 | 126888190 | 126888709 | 8 | 30 | CBS |
| chr15 | 27783853 | 27784356 | 7 | 1023 | CBS |
| chr19 | 32703187 | 32703693 | 7 | 610 | CBS |
| chr11 | 69750753 | 69751263 | 7 | 580 | CBS |
| chr9 | 131914502 | 131915008 | 7 | 345 | CBS |
| chr2 | 65853977 | 65854487 | 7 | 332 | CBS |
| chr6 | 27247206 | 27247715 | 7 | 280 | CBS |
| chr15 | 33693648 | 33694159 | 7 | 274 | CBS |
| chr4 | 173907279 | 173907789 | 7 | 234 | CBS |
| chr7 | 7769275 | 7769801 | 7 | 120 | CBS |
| chr19 | 2121817 | 2122322 | 7 | 117 | CBS |
| chr8 | 94762064 | 94762573 | 6 | 2427 | CBS |
| chr16 | 59245045 | 59245555 | 6 | 496 | CBS |
| chr2 | 3579370 | 3579875 | 6 | 341 | CBS |
| chr1 | 186338264 | 186338773 | 6 | 308 | CBS |
| chr6 | 40451542 | 40452052 | 6 | 245 | CBS |
| chr7 | 131308704 | 131309211 | 6 | 220 | CBS |
| chr11 | 49963855 | 49964372 | 6 | 208 | CBS |
| chr11 | 31515788 | 31516297 | 6 | 186 | CBS |
| chr6 | 143628747 | 143629252 | 6 | 184 | CBS |
| chr7 | 91394256 | 91394759 | 6 | 177 | CBS |
| chr9 | 102600198 | 102600701 | 6 | 140 | CBS |
| chr5 | 177371842 | 177372363 | 6 | 109 | CBS |
| chr6 | 130485685 | 130486199 | 6 | 101 | CBS |
| chr17 | 79978041 | 79978546 | 6 | 85 | CBS |
| chr6 | 143636867 | 143637377 | 6 | 71 | CBS |
| chrX | 72272282 | 72272791 | 6 | 69 | CBS |
| chr13 | 114101805 | 114102315 | 5 | 820 | CBS |
| chr4 | 76774790 | 76775295 | 5 | 809 | CBS |
| chr3 | 46411418 | 46411925 | 5 | 766 | CBS |
| chr10 | 55973993 | 55974499 | 5 | 745 | CBS |
| chr9 | 38254525 | 38255028 | 5 | 488 | CBS |
| chr9 | 18557072 | 18557577 | 5 | 410 | CBS |
| chr3 | 46445017 | 46445531 | 5 | 380 | CBS |
| chr18 | 63835995 | 63836497 | 5 | 339 | CBS |
| chr5 | 127232193 | 127232697 | 5 | 317 | CBS |
| chr1 | 112168534 | 112169040 | 5 | 294 | CBS |
| chr20 | 32614709 | 32615211 | 5 | 292 | CBS |
| chr2 | 80914457 | 80914959 | 5 | 284 | CBS |
| chr10 | 2406025 | 2406532 | 5 | 272 | CBS |
| chr10 | 28696454 | 28696961 | 5 | 272 | CBS |
| chr14 | 88256869 | 88257375 | 5 | 251 | CBS |
| chr19 | 19505880 | 19506387 | 5 | 240 | CBS |
| chr9 | 70388652 | 70389158 | 5 | 235 | CBS |
| chr9 | 33409401 | 33409908 | 5 | 230 | CBS |
| chr17 | 38415258 | 38415770 | 5 | 228 | CBS |
| chr1 | 40698677 | 40699183 | 5 | 219 | CBS |
| chr8 | 136204368 | 136204872 | 5 | 211 | CBS |
| chr1 | 216502468 | 216502974 | 5 | 209 | CBS |
| chr7 | 26267708 | 26268214 | 5 | 202 | CBS |
| chr17 | 49401535 | 49402043 | 5 | 193 | CBS |
| chr12 | 12787084 | 12787589 | 5 | 171 | CBS |
| chr4 | 1693018 | 1693534 | 5 | 162 | CBS |
| chr8 | 38858536 | 38859046 | 5 | 150 | CBS |
| chr4 | 2620355 | 2620855 | 5 | 127 | CBS |
| chr4 | 109557413 | 109557919 | 5 | 126 | CBS |
| chr19 | 28522506 | 28523013 | 5 | 119 | CBS |
| chr11 | 86139833 | 86140336 | 5 | 107 | CBS |
| chr9 | 123514549 | 123515054 | 5 | 103 | CBS |
| chr10 | 86576951 | 86577457 | 5 | 78 | CBS |
| chrX | 29244651 | 29245157 | 5 | 63 | CBS |
| chr11 | 36240842 | 36241345 | 5 | 49 | CBS |
| chr15 | 96641850 | 96642361 | 5 | 39 | CBS |
| chr9 | 89213638 | 89214142 | 5 | 38 | CBS |
| chr1 | 200635695 | 200636199 | 4 | 503 | CBS |
| chr14 | 38655983 | 38656486 | 4 | 451 | CBS |
| chr15 | 89371851 | 89372356 | 4 | 358 | CBS |
| chr4 | 2869887 | 2870392 | 4 | 354 | CBS |
| chr6 | 137829231 | 137829737 | 4 | 342 | CBS |
| chr11 | 77252689 | 77253194 | 4 | 326 | CBS |
| chr15 | 51628367 | 51628874 | 4 | 248 | CBS |
| chr10 | 53066645 | 53067158 | 4 | 224 | CBS |
| chr3 | 15452244 | 15452751 | 4 | 213 | CBS |
| chr3 | 65002198 | 65002704 | 4 | 138 | CBS |
| chr1 | 60997000 | 60997510 | 4 | 130 | CBS |
| chr12 | 54236355 | 54237067 | 4 | 117 | CBS |
| chr2 | 173548865 | 173549369 | 4 | 113 | CBS |
| chr3 | 46393593 | 46394096 | 4 | 112 | CBS |
| chr6 | 156725581 | 156726092 | 4 | 101 | CBS |
| chr11 | 66915449 | 66915954 | 4 | 100 | CBS |
| chr4 | 1055772 | 1056284 | 4 | 95 | CBS |
| chr1 | 184825832 | 184826338 | 4 | 87 | CBS |
| chr2 | 69215725 | 69216234 | 4 | 83 | CBS |
| chr10 | 129225376 | 129225883 | 4 | 73 | CBS |
| chr8 | 69492701 | 69493206 | 4 | 73 | CBS |
| chr8 | 68587575 | 68588079 | 4 | 71 | CBS |
| chr5 | 139124212 | 139124716 | 4 | 63 | CBS |
| chr6 | 15884860 | 15885550 | 4 | 61 | CBS |
| chr21 | 26072559 | 26073063 | 4 | 58 | CBS |
| chr3 | 153091026 | 153091529 | 4 | 55 | CBS |
| chr3 | 50861382 | 50861886 | 4 | 46 | CBS |
| chr7 | 108610938 | 108611440 | 4 | 43 | CBS |
| chr19 | 17219771 | 17220274 | 4 | 26 | CBS |
| chr15 | 78960842 | 78961356 | 4 | 18 | CBS |
| chr3 | 165425162 | 165425675 | 4 | 16 | CBS |
| chr7 | 157319162 | 157319668 | 4 | 11 | CBS |
| chr11 | 113417981 | 113418481 | 3 | 2848 | CBS |
| chr8 | 141479140 | 141479920 | 3 | 1404 | CBS |
| chr5 | 11169204 | 11169704 | 3 | 724 | CBS |
| chr10 | 112920191 | 112920700 | 3 | 676 | CBS |
| chr11 | 112588300 | 112588810 | 3 | 621 | CBS |
| chr4 | 18234048 | 18234552 | 3 | 458 | CBS |
| chr17 | 4380511 | 4381020 | 3 | 411 | CBS |
| chr4 | 11274428 | 11274929 | 3 | 381 | CBS |
| chr15 | 29948282 | 29948787 | 3 | 352 | CBS |
| chr18 | 36530300 | 36530800 | 3 | 295 | CBS |
| chrX | 153791109 | 153791615 | 3 | 279 | CBS |
| chr12 | 18509306 | 18509816 | 3 | 266 | CBS |
| chr17 | 45218569 | 45219074 | 3 | 185 | CBS |
| chr4 | 42518552 | 42519056 | 3 | 176 | CBS |
| chr6 | 155540040 | 155540544 | 3 | 147 | CBS |
| chrX | 115645818 | 115646318 | 3 | 146 | CBS |
| chr10 | 44544941 | 44545450 | 3 | 143 | CBS |
| chr17 | 48063737 | 48064241 | 3 | 115 | CBS |
| chr5 | 97535476 | 97535976 | 3 | 109 | CBS |

TABLE 4-continued

CAST-Seq analysis for CCR5 targeting CRISPR-Cas9 nuclease

| Chromosome | Start | End | Hits | Reads | Category |
|---|---|---|---|---|---|
| chr3 | 46348421 | 46348930 | 3 | 106 | CBS |
| chr2 | 239988540 | 239989042 | 3 | 95 | CBS |
| chr4 | 100650839 | 100651349 | 3 | 95 | CBS |
| chr13 | 97026065 | 97026568 | 3 | 88 | CBS |
| chr7 | 37672389 | 37672898 | 3 | 85 | CBS |
| chr7 | 23678576 | 23679085 | 3 | 83 | CBS |
| chr8 | 129635414 | 129635916 | 3 | 75 | CBS |
| chr6 | 84500191 | 84500694 | 3 | 64 | CBS |
| chr6 | 27090092 | 27090598 | 3 | 63 | CBS |
| chr11 | 98499993 | 98500495 | 3 | 55 | CBS |
| chr19 | 9555661 | 9556162 | 3 | 44 | CBS |
| chr4 | 105211836 | 105212339 | 3 | 39 | CBS |
| chr13 | 101369378 | 101369883 | 3 | 36 | CBS |
| chr13 | 56755987 | 56756487 | 3 | 32 | CBS |
| chr2 | 108338695 | 108339216 | 3 | 27 | CBS |
| chr1 | 75920748 | 75921253 | 3 | 21 | CBS |
| chr1 | 185205447 | 185205953 | 3 | 17 | CBS |
| chr13 | 67889173 | 67889687 | 3 | 16 | CBS |
| chr16 | 69102160 | 69102664 | 3 | 12 | CBS |
| chr17 | 82038731 | 82039235 | 2 | 477 | CBS |
| chr14 | 20631760 | 20632273 | 2 | 431 | CBS |
| chr4 | 43014401 | 43014902 | 2 | 316 | CBS |
| chrX | 118259173 | 118259681 | 2 | 256 | CBS |
| chr7 | 17621451 | 17621951 | 2 | 238 | CBS |
| chr3 | 74033894 | 74034397 | 2 | 232 | CBS |
| chr7 | 98990484 | 98990986 | 2 | 212 | CBS |
| chr4 | 26631521 | 26632024 | 2 | 203 | CBS |
| chr10 | 24406690 | 24407193 | 2 | 188 | CBS |
| chr1 | 151017119 | 151017621 | 2 | 179 | CBS |
| chr19 | 33134450 | 33134950 | 2 | 165 | CBS |
| chrM | 7851 | 8360 | 2 | 159 | CBS |
| chr5 | 166609122 | 166609625 | 2 | 157 | CBS |
| chr1 | 34453057 | 34453560 | 2 | 155 | CBS |
| chr18 | 45147024 | 45147531 | 2 | 146 | CBS |
| chr7 | 152294192 | 152294697 | 2 | 138 | CBS |
| chr20 | 11786155 | 11786665 | 2 | 130 | CBS |
| chr3 | 126350843 | 126351346 | 2 | 122 | CBS |
| chr9 | 80433013 | 80433513 | 2 | 118 | CBS |
| chr15 | 94746835 | 94747338 | 2 | 111 | CBS |
| chr5 | 87461581 | 87462083 | 2 | 101 | CBS |
| chr6 | 115217939 | 115218443 | 2 | 91 | CBS |
| chr1 | 157064187 | 157064689 | 2 | 80 | CBS |
| chr2 | 180392626 | 180393127 | 2 | 76 | CBS |
| chr9 | 42951103 | 42951605 | 2 | 70 | CBS |
| chr5 | 153617451 | 153617951 | 2 | 68 | CBS |
| chr2 | 180755987 | 180756487 | 2 | 62 | CBS |
| chr7 | 15108412 | 15108914 | 2 | 43 | CBS |
| chrX | 33590983 | 33591485 | 2 | 35 | CBS |
| chr7 | 50689655 | 50690158 | 2 | 32 | CBS |
| chr16 | 57658360 | 57658863 | 2 | 31 | CBS |
| chr7 | 13091707 | 13092209 | 2 | 29 | CBS |
| chr21 | 41109456 | 41109957 | 2 | 28 | CBS |
| chr7 | 15987330 | 15987832 | 2 | 28 | CBS |
| chr18 | 50291373 | 50291873 | 2 | 22 | CBS |
| chr6 | 138450255 | 138450757 | 2 | 20 | CBS |
| chr6 | 74442580 | 74443080 | 2 | 19 | CBS |
| chr8 | 472578 | 473082 | 2 | 19 | CBS |
| chr3 | 95094312 | 95094816 | 2 | 16 | CBS |
| chr6 | 119200268 | 119200768 | 2 | 16 | CBS |
| chr20 | 23519480 | 23519982 | 2 | 12 | CBS |

TABLE 5

Sensitivity of CAST-Seq

| Sample | Method | ng/reaction | Positive reads | Copies/500 ng |
|---|---|---|---|---|
| CCR5/CCR2 untreated cells | CAST-Seq | 500 | 60 | — |
| | ddPCR | 0.003 | 4/163,185 | 9.8 |
| CCR5/CCR2 CRISPR-Cas9 edited cells | CAST-Seq | 500 | 63,011 | — |
| | ddPCR | 0.003 | 174/33,325 | 1280 |

Droplet digital PCR (ddPCR) was used to determine the number of large CCR5/CCR2 deletion events between the CCR5 and the CCR2 loci.

TABLE 6

CAST-Seq analysis for VEGFA targeting CRISPR-Cas9 nuclease

| Chromosome | Start | End | Hits | Reads | Category |
|---|---|---|---|---|---|
| chr6 | 43748797 | 43786167 | 6248 | 996445 | ON-TARGET |
| chr14 | 65102179 | 65102710 | 49 | 1646 | OFF-TARGET |
| chr22 | 37266517 | 37267041 | 34 | 1417 | OFF-TARGET |
| chr5 | 90144882 | 90145413 | 27 | 1572 | OFF-TARGET |
| chr5 | 116098720 | 116099230 | 9 | 243 | OFF-TARGET |
| chr20 | 59400339 | 59400861 | 9 | 148 | OFF-TARGET |
| chr6 | 43737908 | 43739102 | 8 | 493 | OFF-TARGET |
| chr11 | 18369652 | 18370170 | 8 | 156 | OFF-TARGET |
| chr19 | 40601908 | 40602418 | 8 | 24 | OFF-TARGET |
| chr3 | 179462091 | 179462601 | 7 | 233 | OFF-TARGET |
| chr16 | 12170504 | 12171007 | 7 | 84 | OFF-TARGET |
| chr12 | 58444469 | 58444973 | 6 | 31 | OFF-TARGET |
| chr6 | 39060603 | 39061111 | 5 | 126 | OFF-TARGET |
| chr6 | 43720476 | 43720979 | 4 | 97 | OFF-TARGET |
| chr11 | 69083417 | 69083928 | 3 | 129 | OFF-TARGET |
| chr10 | 113678795 | 113679299 | 3 | 11 | OFF-TARGET |
| chr18 | 55588355 | 55588859 | 2 | 74 | OFF-TARGET |
| chr10 | 97000584 | 97001084 | 2 | 54 | OFF-TARGET |
| chr11 | 122681489 | 122681989 | 2 | 39 | OFF-TARGET |
| chr14 | 61611810 | 61612312 | 2 | 21 | OFF-TARGET |
| chr5 | 11938880 | 11939383 | 2 | 12 | OFF-TARGET |
| chr10 | 128219323 | 128219823 | 2 | 11 | OFF-TARGET |
| chr16 | 25475787 | 25476289 | 2 | 11 | OFF-TARGET |
| chr6 | 42465570 | 42466081 | 4 | 315 | HR |
| chr6 | 43741170 | 43743375 | 11 | 599 | CBS |
| chr8 | 133122122 | 133122635 | 8 | 433 | CBS |
| chr3 | 43438528 | 43439033 | 8 | 211 | CBS |
| chr6 | 43187467 | 43187977 | 7 | 193 | CBS |
| chr6 | 43733353 | 43733861 | 7 | 191 | CBS |
| chr11 | 132132426 | 132132932 | 7 | 98 | CBS |
| chr17 | 8611719 | 8612229 | 6 | 337 | CBS |
| chr6 | 43715825 | 43716338 | 6 | 206 | CBS |
| chr12 | 91984719 | 91985230 | 6 | 149 | CBS |
| chr9 | 80241133 | 80241648 | 6 | 141 | CBS |

TABLE 6-continued

CAST-Seq analysis for VEGFA targeting CRISPR-Cas9 nuclease

| Chromosome | Start | End | Hits | Reads | Category |
|---|---|---|---|---|---|
| chr12 | 120678790 | 120679309 | 6 | 123 | CBS |
| chrX | 126695885 | 126696392 | 5 | 505 | CBS |
| chr2 | 144496514 | 144497032 | 5 | 285 | CBS |
| chr3 | 51431062 | 51431579 | 5 | 223 | CBS |
| chr5 | 93772512 | 93773014 | 5 | 189 | CBS |
| chrUn_KI270442v1 | 98918 | 99420 | 5 | 96 | CBS |
| chr20 | 16983569 | 16984078 | 5 | 73 | CBS |
| chr11 | 65289784 | 65290286 | 5 | 71 | CBS |
| chr11 | 62744864 | 62745368 | 4 | 332 | CBS |
| chr10 | 62979116 | 62979625 | 4 | 246 | CBS |
| chr8 | 103827952 | 103828465 | 4 | 149 | CBS |
| chrX | 37912288 | 37912790 | 4 | 120 | CBS |
| chr8 | 51018324 | 51018841 | 4 | 99 | CBS |
| chr6 | 81829314 | 81829818 | 4 | 88 | CBS |
| chr11 | 46891576 | 46892079 | 4 | 62 | CBS |
| chr4 | 46405134 | 46405638 | 4 | 45 | CBS |
| chr6 | 31492043 | 31492545 | 3 | 521 | CBS |
| chr2 | 86112989 | 86113496 | 3 | 227 | CBS |
| chr14 | 24347314 | 24347817 | 3 | 215 | CBS |
| chr3 | 129911170 | 129911671 | 3 | 142 | CBS |
| chr3 | 158845758 | 158846260 | 3 | 128 | CBS |
| chr15 | 70227078 | 70227584 | 3 | 108 | CBS |
| chr12 | 124923985 | 124924489 | 3 | 72 | CBS |
| chr9 | 112200162 | 112200664 | 3 | 71 | CBS |
| chr7 | 51813287 | 51813796 | 3 | 65 | CBS |
| chr1 | 109067369 | 109067871 | 3 | 61 | CBS |
| chr22 | 27094649 | 27095151 | 3 | 43 | CBS |
| chr6 | 108630850 | 108631354 | 3 | 36 | CBS |
| chr1 | 110417674 | 110418189 | 3 | 28 | CBS |
| chr21 | 45699101 | 45699603 | 3 | 23 | CBS |
| chr16 | 75303846 | 75304352 | 3 | 21 | CBS |
| chr5 | 18617756 | 18618262 | 2 | 292 | CBS |
| chr11 | 69569487 | 69569990 | 2 | 268 | CBS |
| chr19 | 12369785 | 12370286 | 2 | 86 | CBS |
| chr22 | 38055609 | 38056112 | 2 | 78 | CBS |
| chr11 | 3468924 | 3469431 | 2 | 50 | CBS |
| chr19 | 33384998 | 33385498 | 2 | 50 | CBS |
| chr5 | 62393455 | 62393960 | 2 | 48 | CBS |
| chr3 | 171773292 | 171773802 | 2 | 29 | CBS |
| chr17 | 12195155 | 12195655 | 2 | 27 | CBS |
| chr20 | 57997602 | 57998104 | 2 | 20 | CBS |
| chr6 | 47302001 | 47302503 | 2 | 16 | CBS |
| chr6 | 43729146 | 43729649 | 2 | 14 | CBS |
| chr17 | 21170726 | 21171226 | 2 | 13 | CBS |

TABLE 7

CAST-Seq analysis for FANCF targeting CRISPR-Cas9 nuclease

| Chromosome | Start | End | Hits | Reads | Category |
|---|---|---|---|---|---|
| chr11 | 22606881 | 22632976 | 16940 | 1194160 | ON-TARGET |
| chr8 | 107462104 | 107462619 | 3 | 202 | OFF-TARGET |
| chr17 | 75942773 | 75943281 | 8 | 427 | HR |
| chr11 | 547497 | 548003 | 8 | 13 | HR |
| chr10 | 3343323 | 3343830 | 6 | 334 | HR |
| chr6 | 54512069 | 54512584 | 5 | 602 | HR |
| chr22 | 31700499 | 31700999 | 4 | 508 | HR |
| chr16 | 65201096 | 65201596 | 2 | 29 | HR |
| chr11 | 22638379 | 22640795 | 16 | 756 | CBS |
| chr12 | 118006840 | 118007350 | 14 | 327 | CBS |
| chr11 | 22635293 | 22635993 | 13 | 1591 | CBS |
| chr17 | 45061400 | 45061910 | 11 | 869 | CBS |
| chr11 | 22603294 | 22604583 | 11 | 306 | CBS |
| chr2 | 217749840 | 217750351 | 11 | 200 | CBS |
| chr10 | 92944396 | 92944911 | 10 | 628 | CBS |
| chr11 | 22596928 | 22597439 | 10 | 513 | CBS |
| chr4 | 170721395 | 170721913 | 10 | 245 | CBS |
| chr5 | 223850 | 224355 | 10 | 112 | CBS |
| chr2 | 156410822 | 156411330 | 9 | 564 | CBS |
| chr11 | 22553782 | 22554292 | 9 | 399 | CBS |
| chr3 | 131301701 | 131302212 | 9 | 184 | CBS |
| chr11 | 62226588 | 62227098 | 9 | 172 | CBS |

TABLE 7-continued

CAST-Seq analysis for FANCF targeting CRISPR-Cas9 nuclease

| Chromosome | Start | End | Hits | Reads | Category |
|---|---|---|---|---|---|
| chr15 | 74789553 | 74790064 | 8 | 1597 | CBS |
| chr2 | 137754238 | 137754752 | 8 | 537 | CBS |
| chr11 | 22493017 | 22493531 | 8 | 437 | CBS |
| chr14 | 37848648 | 37849160 | 8 | 361 | CBS |
| chr5 | 117503633 | 117504145 | 8 | 236 | CBS |
| chr3 | 141960302 | 141960813 | 8 | 183 | CBS |
| chr9 | 134110671 | 134111182 | 7 | 853 | CBS |
| chr6 | 64592782 | 64593296 | 7 | 833 | CBS |
| chr15 | 41979815 | 41980319 | 7 | 634 | CBS |
| chr1 | 234873070 | 234873586 | 7 | 631 | CBS |
| chr11 | 22497191 | 22497702 | 7 | 516 | CBS |
| chr1 | 240683448 | 240683973 | 7 | 346 | CBS |
| chr10 | 16143699 | 16144212 | 7 | 221 | CBS |
| chr1 | 78612968 | 78613479 | 7 | 202 | CBS |
| chrX | 96728443 | 96728954 | 6 | 530 | CBS |
| chr11 | 22546650 | 22547161 | 6 | 310 | CBS |
| chr2 | 129780736 | 129781243 | 6 | 273 | CBS |
| chr11 | 22170550 | 22171062 | 6 | 260 | CBS |
| chr11 | 62851806 | 62852311 | 6 | 117 | CBS |
| chr16 | 173343 | 173857 | 5 | 1377 | CBS |
| chr8 | 142938854 | 142939365 | 5 | 959 | CBS |
| chr20 | 21331851 | 21332361 | 5 | 679 | CBS |
| chr11 | 22580420 | 22580932 | 5 | 424 | CBS |
| chr7 | 102837794 | 102838306 | 5 | 411 | CBS |
| chr11 | 22566342 | 22566853 | 5 | 233 | CBS |
| chr1 | 247258418 | 247258927 | 5 | 226 | CBS |
| chr12 | 45103309 | 45103828 | 5 | 223 | CBS |
| chr14 | 105323378 | 105323887 | 5 | 139 | CBS |
| chr1 | 178305158 | 178305668 | 5 | 47 | CBS |
| chr10 | 90062787 | 90063289 | 4 | 568 | CBS |
| chr16 | 2350790 | 2351306 | 4 | 310 | CBS |
| chr7 | 75678856 | 75679361 | 4 | 167 | CBS |
| chr3 | 172715492 | 172716001 | 4 | 143 | CBS |
| chr1 | 235016437 | 235016944 | 4 | 74 | CBS |
| chr6 | 18644615 | 18645122 | 4 | 69 | CBS |
| chr18 | 46622512 | 46623014 | 3 | 1106 | CBS |
| chr17 | 40424371 | 40424885 | 3 | 583 | CBS |
| chr5 | 149868431 | 149868932 | 3 | 382 | CBS |
| chr11 | 40812298 | 40812806 | 3 | 336 | CBS |
| chr3 | 50181773 | 50182276 | 3 | 319 | CBS |
| chr22 | 45412128 | 45412628 | 3 | 270 | CBS |
| chr1 | 53577913 | 53578425 | 3 | 252 | CBS |
| chr4 | 134558964 | 134559473 | 3 | 251 | CBS |
| chr18 | 71341064 | 71341570 | 3 | 247 | CBS |
| chr18 | 44811004 | 44811516 | 3 | 212 | CBS |
| chr11 | 30496682 | 30497192 | 3 | 206 | CBS |
| chr10 | 110052643 | 110053143 | 3 | 120 | CBS |
| chr10 | 2906798 | 2907498 | 3 | 92 | CBS |
| chr3 | 122911294 | 122911794 | 3 | 66 | CBS |
| chr13 | 24842172 | 24842680 | 3 | 52 | CBS |
| chr11 | 20802893 | 20803396 | 3 | 41 | CBS |
| chr2 | 105413692 | 105414194 | 3 | 26 | CBS |
| chr1 | 206110190 | 206110694 | 3 | 13 | CBS |
| chr2 | 121678953 | 121679461 | 3 | 9 | CBS |
| chr17 | 38879882 | 38880386 | 2 | 660 | CBS |
| chr4 | 138331185 | 138331693 | 2 | 555 | CBS |
| chr8 | 127002239 | 127002739 | 2 | 303 | CBS |
| chr13 | 82512617 | 82513120 | 2 | 258 | CBS |
| chr11 | 22526098 | 22526600 | 2 | 247 | CBS |
| chr21 | 32488958 | 32489461 | 2 | 220 | CBS |
| chr4 | 124168649 | 124169153 | 2 | 149 | CBS |
| chr11 | 22334210 | 22334711 | 2 | 147 | CBS |
| chr11 | 30548665 | 30549165 | 2 | 75 | CBS |
| chr11 | 66802270 | 66802770 | 2 | 41 | CBS |
| chr18 | 30656154 | 30656661 | 2 | 31 | CBS |
| chr16 | 87951936 | 87952438 | 2 | 24 | CBS |
| chr21 | 14495238 | 14495740 | 2 | 22 | CBS |
| chr5 | 159229053 | 159229555 | 2 | 22 | CBS |
| chr10 | 8393633 | 8394133 | 2 | 17 | CBS |
| chr13 | 64752705 | 64753213 | 2 | 16 | CBS |
| chr19 | 39397176 | 39397676 | 2 | 13 | CBS |
| chr5 | 153083290 | 153083792 | 2 | 13 | CBS |
| chr11 | 22666156 | 22666659 | 2 | 11 | CBS |

TABLE 8

Software used for CAST-Seq

| Software | Version | Usage | Alternative |
|---|---|---|---|
| FLASh (https://ccb.jhu.edu/software/FLASH/) | 1.2.11 | pairing reads | Bbmerge (https://jgi.doe.gov/data-and-tools/bbtools/) |
| Bbmap (https://jgi.doe.gov/data-and-tools/bbtools/) | 38.22 | selection of designer nuclease target sites, linker and adapter trimming | Trimmomatic (http://www.usadellab.org/cms/?page=trimmomatic) |
| Bowite2 (http://bowtie-bio.sourceforge.net/bowtie2/index.shtml) | 2.3.4.2 | Alignment to hg38 genome | BWA (http://bio-bwa.sourceforge.net/index.shtml) |
| samtools (http://samtools.sourceforge.net) | 1.9 | SAM to BAM conversion | Picard (https://broadinstitute.github.io/picard/) |
| bedtools (https://bedtools.readthedocs.io/en/latest/) | 2.27.1 | BAM to Bed conversion, random sequences generation | BEDOPS (https://bedops.readthedocs.io/en/latest/) |

TABLE 9

R package used for CAST-Seq

| Software | Version | URL | Usage |
|---|---|---|---|
| BSgenome.*Hsapiens*.UCSC.hg38 | 1.4.1 | http://bioconductor.org/packages/release/data/annotation/html/BSgenome.*Hsapiens*.UCSC.hg38.html | get sequence from genomic coordinates |
| Biostrings | 2.46.0 | https://bioconductor.org/packages/release/bioc/html/Biostrings.html | align sequence to guide-RNA |
| ChIPseeker | 1.14.2 | https://bioconductor.org/packages/release/bioc/html/ChIPseeker.html | gene annotation of translocation sites |
| TxDb.*Hsapiens*.UCSC.hg38.knownGene | 3.2.2 | https://bioconductor.org/packages/release/data/annotation/html/TxDb.*Hsapiens*.UCSC.hg38.knownGene.html | known gene coordinates and gene regions |
| org.Hs.eg.db | 3.5.0 | https://bioconductor.org/packages/release/data/annotation/html/org.Hs.eg.db.html | match gene symbol and entrez ID |
| biomaRt | 2.34.2 | https://bioconductor.org/packages/release/bioc/html/biomaRt.html | retrieve oncogene TSS |

TABLE 10

Scoring Matrix

| | A | C | G | T | M | R | W | S | Y | K | V | H | D | B | N | BULGE |
|---|---|---|---|---|---|---|---|---|---|---|---|---|---|---|---|---|
| A | 1 | −1 | −1 | −1 | 0 | 0 | 0 | −1 | −1 | −1 | −0.333 | −0.333 | −0.333 | −1 | −0.5 | −1 |
| C | −1 | 1 | −1 | −1 | 0 | −1 | −1 | 0 | 0 | −1 | −0.333 | −0.333 | −1 | −0.333 | −0.5 | −1 |
| G | −1 | −1 | 1 | −1 | −1 | 0 | −1 | 0 | −1 | 0 | −0.333 | −1 | −0.333 | −0.333 | −0.5 | −1 |
| T | −1 | −1 | −1 | 1 | −1 | −1 | 0 | −1 | 0 | 0 | −1 | −0.333 | −0.333 | −0.333 | −0.5 | −1 |
| M | 0 | 0 | −1 | −1 | 0 | −0.5 | −0.5 | −0.5 | −0.5 | −1 | −0.333 | −0.333 | −0.667 | −0.667 | −0.5 | −1 |
| R | 0 | −1 | 0 | −1 | −0.5 | 0 | −0.5 | −0.5 | −1 | −0.5 | −0.333 | −0.667 | −0.333 | −0.667 | −0.5 | −1 |
| W | 0 | −1 | −1 | 0 | −0.5 | −0.5 | 0 | −1 | −0.5 | −0.5 | −0.667 | −0.333 | −0.333 | −0.667 | −0.5 | −1 |
| S | −1 | 0 | 0 | −1 | −0.5 | −0.5 | −1 | 0 | −0.5 | −0.5 | −0.333 | −0.667 | −0.667 | −0.333 | −0.5 | −1 |
| Y | −1 | 0 | −1 | 0 | −0.5 | −1 | −0.5 | −0.5 | 0 | −0.5 | −0.667 | −0.333 | −0.667 | −0.333 | −0.5 | −1 |

TABLE 10-continued

Scoring Matrix

| | A | C | G | T | M | R | W | S | Y | K | V | H | D | B | N | BULGE |
|---|---|---|---|---|---|---|---|---|---|---|---|---|---|---|---|---|
| K | -1 | -1 | 0 | 0 | -1 | -0.5 | -0.5 | -0.5 | -0.5 | 0 | -0.66667 | -0.66667 | -0.33333 | -0.33333 | -1 | 0.5 |
| V | -0.33333 | 0.33333 | 0.33333 | -1 | 0.33333 | 0.33333 | -0.66667 | 0.33333 | -0.66667 | -0.66667 | 0.33333 | 0.55556 | 0.55556 | 0.55556 | -0.5 | -1 |
| H | -0.33333 | 0.33333 | -1 | 0.33333 | 0.33333 | -0.66667 | 0.33333 | -0.66667 | 0.33333 | -0.66667 | 0.55556 | 0.33333 | 0.55556 | 0.55556 | -0.5 | -1 |
| D | 0.33333 | -1 | 0.33333 | 0.33333 | -0.66667 | 0.33333 | 0.33333 | -0.66667 | -0.66667 | 0.33333 | 0.55556 | 0.55556 | 0.33333 | 0.55556 | -0.5 | -1 |
| B | -1 | 0.33333 | 0.33333 | 0.33333 | -0.66667 | -0.66667 | -0.66667 | 0.33333 | 0.33333 | 0.33333 | 0.55556 | 0.55556 | 0.55556 | 0.33333 | -0.5 | -1 |
| N | -0.5 | -0.5 | -0.5 | -0.5 | -0.5 | -0.5 | -0.5 | -0.5 | -0.5 | -0.5 | -0.5 | -0.5 | -0.5 | -0.5 | -0.5 | -1 |
| BULGE | -1 | -1 | -1 | -1 | -1 | -1 | -1 | -1 | -1 | -1 | -1 | -1 | -1 | -1 | -1 | n/a |

Scoring matrix of nucleotide substitution used for the alignment of translocation sites against the target site sequence, including weights for mismatch and bulges (insertions/deletions).

IUPAC code is used. A, adenine; C, cytosine; G, guanine; T (or U), thymine (or uracil); R, A or G; Y, C or T; S, G or C; W, A or T; K, G or T; M, A or C; B, C or G or T; D, A or G or T; H, A or C or T; V, A or C or G; N, any base; n/a, not applicable.

TABLE 11

Primer Design for HBB Target Site (targeted by TALEN)

| FUNCTION | | SEQUENCE 5'-3' |
|---|---|---|
| TARGET SEQUENCE | | TGATAGGCACTGACTCTCT (left TALEN subunit) (SEQ ID NO: 25) TAAGGGTGGGAAAATAGAC (right TALEN subunit) (SEQ ID NO: 26) |
| CAST-SEQ 1ST PCR | bait decoy for | GTTGGTATCAAGGTTACAAGAC (SEQ ID NO: 27) CTGCTGGTGGTCTACC (SEQ ID NO: 28) |
| CAST-SEQ 2ND PCR | bait nested | GACTGGAGTTCAGACGTGTGCTCTTCCG ATCTGACCAATAGAAACTGGGCATGTGG (SEQ ID NO: 29) |

TABLE 12

Primer Design for CCR5 Target Site 2 (CCR54#2, targeted by CRISPR-Cas9)

| FUNCTION | | SEQUENCE 5'-3' |
|---|---|---|
| TARGET SEQUENCE | | CAATGTGTCAACTCTTGACAGGG (SEQ ID NO: 30) AAACACAGCATGGACGAC (SEQ ID NO: 31) |
| CAST-SEQ 1ST PCR | bait decoy for | CCAGTGGGACTTTGGAAATAC (SEQ ID NO: 32) GCATAGTGAGCCCAGAAG (SEQ ID NO: 33) |
| CAST-SEQ 2ND PCR | decoy rev bait nested | GACTGGAGTTCAGACGTGTGCTCTTCCGAT CTAGGAGGATGATGAAGAAGATTCCAGAG (SEQ ID NO: 34) |

TABLE 13

Primer Design for ddPCR

| Target | Function | | Sequence 5'-3' |
|---|---|---|---|
| CCR5#1 | ddPCR-Edge | For | TTATTATACATCGGAGCCCTGCCAA (SEQ ID NO: 35) |
| | | Rev | TGCTCTTCAGCCTTTTGCAGTTTATCAG (SEQ ID NO: 36) |
| | ddPCR-5' | For | AGTTTGCATTCATGGAGGGCAAC (SEQ ID NO: 37) |
| | | Rev | GGCAGGGCTCCGATGTATAATAATTG (SEQ ID NO: 38) |
| | ddPCR-3' | For | CATGCTGGTCATCCTCATCCTG (SEQ ID NO: 39) |
| | | Rev | CCCAGAAGGGGACAGTAAGAAGG (SEQ ID NO: 40) |
| CCR5#2 | ddPCR-Edge | For | TCCTTCTTACTGTCCCCTTCTGG (SEQ ID NO: 41) |
| | | Rev | AGCAAACACAGCATGGACGAC (SEQ ID NO: 42) |
| | ddPCR-5' | For | CATGCTGGTCATCCTCATCCTG (SEQ ID NO: 43) |
| | | Rev | CCCAGAAGGGGACAGTAAGAAGG (SEQ ID NO: 44) |

TABLE 13-continued

Primer Design for ddPCR

| Target | Function | | Sequence 5'-3' |
|---|---|---|---|
| | ddPCR-3' | For | ATCGATAGGTACCTGGCTGTCG (SEQ ID NO: 45) |
| | | Rev | GTATGGAAAATGAGAGCTGCAGGTG (SEQ ID NO: 46) |
| CCR5#1 & CCR5#2 | ddPCR-GADL1 (Telomere) | For | TGCCAAGGCATCTTACCTCTTCC (SEQ ID NO: 47) |
| | | Rev | GCATCTGGTCTTCTGCTACACTGG (SEQ ID NO: 48) |
| | ddPCR-MYLK (q arm) | For | CAGCCTTGTGATTCATGCTGTCC (SEQ ID NO: 49) |
| | | Rev | GGACTCACCTTCTACTGTCAACTCC (SEQ ID NO: 50) |
| HBB | ddPCR-Edge | For | AGACCAATAGAAACTGGGCATGTGG (SEQ ID NO: 51) |
| | | Rev | ATCACTAAAGGCACCGAGCACT (SEQ ID NO: 52) |
| | ddPCR-5' | For | GGCTCATGGCAAGAAAGTGCTC (SEQ ID NO: 53) |
| | | Rev | CAGTGCAGCTCACTCAGTGTG (SEQ ID NO: 54) |

TABLE 13-continued

Primer Design for ddPCR

| Target | Function | | Sequence 5'-3' |
|---|---|---|---|
| | ddPCR-3' | For | CTGAGGAGAAGTCTGCCGTTAC (SEQ ID NO: 55) |
| | | Rev | CCACATGCCCAGTTTCTATTGGT (SEQ ID NO: 56) |
| | ddPCR-CARS (Telomere) | For | GGGCCAGGGAAGTGTATGATG (SEQ ID NO: 57) |
| | | Rev | ACAGACATCAGTGCCATTGCG (SEQ ID NO: 58) |
| | ddPCR-PODL1 (q arm) | For | GCAGGTTCAGTCCCTCTTGG (SEQ ID NO: 59) |
| | | Rev | TGCTTGGCCTATGGACAGTTG (SEQ ID NO: 60) |
| Common Target | ddPCR-RAD1 (ctl.) | For | CCTTCAGCTCTGTGGTGACG (SEQ ID NO: 61) |
| | | Rev | CCCTTCTCAGCAAAGTCCCTG (SEQ ID NO: 62) |
| | ddPCR-STAT3 (ctl.) | For | ACTCTCACGGACGAGGAGC (SEQ ID NO: 63) |
| | | Rev | CAGTTTTCTAGCCGATCTAGGCAG (SEQ ID NO: 64) |

The invention claimed is:

1. A method for high-throughput detection of genome-wide modifications in a nucleic acid genome obtained from a cell or tissue caused by the activity of a designer nuclease, said method comprising the following steps:
   a. extracting the genomic DNA from cells that were exposed to a designer nuclease under conditions which allow the designer nuclease to introduce a DNA double-strand break (DSB) into the genomic DNA of the cell at a designer nuclease target site,
   b. fragmenting the nucleic acid to obtain random fragments,
   c. performing an end repair in order to obtain an end-repaired fragment having ends with a protruding A at the 3' end
   d. ligating with short linkers to the protruding ends of said end-repaired fragment to yield a ligated fragment
   e. performing a first nucleic acid amplification reaction which is a polymerase chain reaction with (i) at least one linker primer having a sequence complementary to the sequence of said short linker; (ii) at least one on-target primer having a sequence complementary to said designer nuclease target site located on said genomic DNA; (iii) at least one decoy primer designed to bind in close proximity to said target site, whereby one of said on-target primer and said decoy primer binds upstream of the target site while the other binds downstream of the target site,
   f. performing a second nucleic acid amplification reaction whereby nested primers having 5'-overhangs are added to the reaction mixture, whereby one of said nested primers is complementary to the target site and the other of site nested primers is complementary to said short linker sequence,
   g. performing a further nucleic acid amplification reaction whereby at least one barcode-containing primer is added to the reaction mixture,
   h. sequencing the barcoded amplification products of step g), and
   i. aligning the sequenced products with suitable bioinformatic means to a reference sequence to identify a chromosomal location that contains a genomic modification based on at least one DNA double-strand break.

2. The method according to claim 1 characterized in that the sequence of at least one of said decoy primers is complementary to a sequence located at least 10 nucleotides downstream of the target site.

3. The method according to claim 1 characterized in that two decoy primers are added to the reaction in step e), whereby the binding site for one of said two decoy primers is located least at least 10 nucleotides downstream of said target site the binding site for the second of the said two decoy primers is located at least 30 nucleotides downstream of said target site.

4. The method according to claim 1 characterized in that a forward on-target primer is located at least 25 nucleotides upstream of the on-target site.

5. The method according to claim 1, wherein said method enables the identification of rare chromosomal aberrations.

6. The method according to claim 1 characterized in that the said at least one decoy primer is designed to bind in close proximity to the target site in an area flanked by a forward on-target primer and a backward linker primer, respectively.

7. The method according to claim 1, wherein said method enables the detection of chromosomal aberrations at the target site and/or at off-target sites.

8. The method according to claim 1 characterized in that the nucleic acid amplification reaction is performed in the area of the target site where the designer nuclease cleaves the nucleic acid.

9. The method according to claim 1 characterized in that the barcode-containing molecule provides a barcode for next generation sequencing.

10. The method according to claim 1 characterized in that the information obtained by the nucleic acid amplification is analyzed by means of bioinformatics comprising the steps of sequence pairing and positive selection for the target sequence.

11. The method according to claim 10 wherein unrelated sequences due to mispriming products or linker products are eliminated.

12. The method according to claim 10 whereby the selected sequences are aligned to a referenced genome.

* * * * *

UNITED STATES PATENT AND TRADEMARK OFFICE
CERTIFICATE OF CORRECTION

| | | |
|---|---|---|
| PATENT NO. | : 11,319,580 B2 | Page 1 of 1 |
| APPLICATION NO. | : 17/277236 | |
| DATED | : May 3, 2022 | |
| INVENTOR(S) | : Toni Cathomen et al. | |

It is certified that error appears in the above-identified patent and that said Letters Patent is hereby corrected as shown below:

In the Specification

- At Column 3, Line 36, replace the word "Illumine" with -- Illumina --.

In the Claims

- At Column 54, Line 26, in Line 4 of Claim 3, delete the first appearance of the word "least".

- At Column 54, Line 27, in Line 5 of Claim 3, replace the first appearance of the word "the" with the word -- and --.

- At Column 54, Line 27, in Line 5 of Claim 3, delete the third appearance of the word "the".

Signed and Sealed this
Sixth Day of December, 2022

Katherine Kelly Vidal
*Director of the United States Patent and Trademark Office*